US012702540B2

(12) United States Patent
Holden et al.

(10) Patent No.: US 12,702,540 B2
(45) Date of Patent: Aug. 11, 2026

(54) COVERED ENDOPROSTHESIS WITH IMPROVED BRANCH DRAINAGE

(71) Applicant: BOSTON SCIENTIFIC SCIMED, INC., Maple Grove, MN (US)

(72) Inventors: Meabh Holden, Dublin (IE); Enda Connaughton, Galway (IE); Richard Crawford, Galway (IE); Gerasimos Rigalos, Galway (IE)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 1247 days.

(21) Appl. No.: 17/576,057

(22) Filed: Jan. 14, 2022

(65) Prior Publication Data

US 2022/0226096 A1 Jul. 21, 2022

Related U.S. Application Data

(60) Provisional application No. 63/138,035, filed on Jan. 15, 2021.

(51) Int. Cl.

*A61F 2/04* (2013.01)
*A61F 2/07* (2013.01)
*A61M 27/00* (2006.01)

(52) U.S. Cl.

CPC .......... *A61F 2/04* (2013.01); *A61F 2002/041* (2013.01); *A61F 2/07* (2013.01); *A61F 2210/0076* (2013.01); *A61F 2230/008* (2013.01); *A61F 2250/001* (2013.01); *A61F 2250/0024* (2013.01); *A61F 2250/0039* (2013.01); *A61F 2250/0098* (2013.01); *A61M 27/002* (2013.01)

(58) Field of Classification Search

CPC ........... A61F 2002/041; A61F 2/04–2002/077; A61F 2250/0024; A61F 2250/0039

See application file for complete search history.

(56) References Cited

U.S. PATENT DOCUMENTS 5,575,818 A 11/1996 Pinchuk
5,741,333 A 4/1998 Frid
(Continued)

FOREIGN PATENT DOCUMENTS

EP 0808138 B1 10/2005
EP 0957773 B1 6/2011
(Continued)

OTHER PUBLICATIONS

International Search Report and Written Opinion dated Sep. 14, 2020 for International Application No. PCT/US2020/037873.
(Continued)

*Primary Examiner* — Rebecca S Preston

(74) *Attorney, Agent, or Firm* — Seager, Tufte & Wickhem, LLP

(57) ABSTRACT

An endoprosthesis may include an expandable framework including a body portion disposed between a first end and a second end, and a bowl portion disposed along the body portion; and a polymeric cover disposed on at least a portion of the expandable framework. The bowl portion may include an inner surface and an outer surface spaced apart radially outward from the inner surface. The bowl portion may extend radially outward from the body portion. The inner surface of the bowl portion may be devoid of the polymeric cover.

16 Claims, 15 Drawing Sheets

(56) References Cited

U.S. PATENT DOCUMENTS

| | | | |
|---|---|---|---|
| 5,876,445 | A | 3/1999 | Andersen et al. |
| 6,264,689 | B1 | 7/2001 | Colgan et al. |
| 6,287,335 | B1 | 9/2001 | Drasler et al. |
| 6,468,303 | B1 | 10/2002 | Amplatz et al. |
| 6,616,675 | B1 | 9/2003 | Evard et al. |
| 6,620,122 | B2 | 9/2003 | Stinson et al. |
| 6,663,663 | B2 | 12/2003 | Kim et al. |
| 7,018,401 | B1 | 3/2006 | Hyodoh et al. |
| 7,115,136 | B2 | 10/2006 | Park et al. |
| 7,311,031 | B2 | 12/2007 | Mccullagh et al. |
| 7,462,192 | B2 | 12/2008 | Norton et al. |
| 7,591,845 | B2 | 9/2009 | Rhim et al. |
| 7,670,367 | B1 | 3/2010 | Chouinard et al. |
| 7,763,011 | B2 | 7/2010 | Ortiz et al. |
| 8,114,147 | B2 | 2/2012 | Wood et al. |
| 8,151,682 | B2 | 4/2012 | Lilburn et al. |
| 8,357,193 | B2 | 1/2013 | Phan et al. |
| 8,454,632 | B2 | 6/2013 | Binmoeller et al. |
| 8,663,314 | B2 | 3/2014 | Wood et al. |
| 8,677,874 | B2 | 3/2014 | Lilburn et al. |
| 9,005,268 | B2 | 4/2015 | Hartley et al. |
| 9,265,634 | B2 | 2/2016 | Brady et al. |
| 9,301,862 | B2 | 4/2016 | Jordan et al. |
| 9,539,126 | B2 | 1/2017 | Walsh et al. |
| 9,675,473 | B2 | 6/2017 | Clerc et al. |
| 10,076,330 | B2 | 9/2018 | Sander et al. |
| 10,085,861 | B2 | 10/2018 | Walsh et al. |
| 10,130,498 | B2 | 11/2018 | Fleury et al. |
| 10,470,910 | B2 | 11/2019 | Folan et al. |
| 2003/0074049 | A1 | 4/2003 | Hoganson et al. |
| 2003/0135265 | A1 | 7/2003 | Stinson |
| 2004/0098099 | A1 | 5/2004 | McCullagh et al. |
| 2004/0230288 | A1 | 11/2004 | Rosenthal |
| 2007/0123922 | A1 | 5/2007 | Cooper et al. |
| 2007/0282453 | A1 | 12/2007 | Weitzner et al. |
| 2009/0082803 | A1 | 3/2009 | Adams et al. |
| 2010/0049307 | A1 | 2/2010 | Ren |
| 2011/0022151 | A1 | 1/2011 | Shin et al. |
| 2011/0054586 | A1 | 3/2011 | Mayberry et al. |
| 2013/0012969 | A1 | 1/2013 | Shin |
| 2014/0081416 | A1 | 3/2014 | Clerc et al. |
| 2015/0148890 | A1 | 5/2015 | Hartley et al. |
| 2016/0058585 | A1 | 3/2016 | Seddon et al. |
| 2016/0081832 | A1 | 3/2016 | Hingston et al. |
| 2016/0113789 | A1 | 4/2016 | Fleury et al. |
| 2016/0128824 | A1 | 5/2016 | Nomura |
| 2016/0302910 | A1 | 10/2016 | Jordan |
| 2017/0086959 | A1 | 3/2017 | Verin et al. |
| 2018/0078745 | A1 | 3/2018 | Gray et al. |
| 2018/0280166 | A1* | 10/2018 | Walsh ....................... A61F 2/91 |
| 2018/0280669 | A1 | 10/2018 | Shlomovitz et al. |
| 2018/0338846 | A1 | 11/2018 | Folan et al. |
| 2019/0117370 | A1 | 4/2019 | Folan |
| 2019/0321204 | A1 | 10/2019 | Folan et al. |
| 2019/0358063 | A1 | 11/2019 | Walsh et al. |
| 2020/0261092 | A1 | 8/2020 | Walsh et al. |
| 2020/0390573 | A1* | 12/2020 | Folan ....................... D04C 3/48 |
| 2022/0062016 | A1 | 3/2022 | Folan et al. |

FOREIGN PATENT DOCUMENTS

| | | | |
|---|---|---|---|
| EP | 2543323 | A1 | 1/2013 |
| EP | 1558149 | B1 | 12/2013 |
| EP | 2754415 | B1 | 5/2015 |
| EP | 2177181 | B1 | 6/2015 |
| GB | 2517401 | A | 2/2015 |
| WO | 9601599 | A1 | 1/1996 |
| WO | 2009140195 | A1 | 11/2009 |
| WO | 2015195893 | A1 | 12/2015 |
| WO | 2020134920 | A1 | 7/2020 |

OTHER PUBLICATIONS

International Search Report and Written Opinion dated Apr. 29, 2022 for International Application No. PCT/US2022/012465.

* cited by examiner 46
44
42
62
60
52
100
120
122
54
106
74
72
50
70
40

COVERED ENDOPROSTHESIS WITH IMPROVED BRANCH DRAINAGE

CROSS REFERENCE TO RELATED APPLICATIONS

This application claims the benefit of U.S. Provisional Patent Application Ser. No. 63/138,035 filed on Jan. 15, 2021, the disclosure of which is incorporated herein by reference.

TECHNICAL FIELD

The present disclosure pertains to medical devices, and methods for manufacturing and/or using medical devices. More particularly, the present disclosure pertains to an improved design for an endoprosthesis or stent.

BACKGROUND

One currently known and/or recommended treatment for relief of biliary blockage in the biliary tree is the placement of a covered endoprosthesis or stent within the restricted body lumen (e.g., the bile duct, the pancreatic duct, etc.), such as that caused by a stricture formation. For example, it may be necessary to open the body lumen (e.g., the bile duct, the pancreatic duct, etc.) to permit passing of bile and stone-related debris to relieve acute painful symptoms. Uncovered metallic endoprostheses or stents are sometimes placed for chronic conditions but are generally not removable. Plastic endoprostheses or stents may be prone to blockage which may require repeat treatment(s) and are sometimes unable to open the stricture that initially caused the blockage of the affected body lumen (e.g., the bile duct, the pancreatic duct, etc.). Additionally, the biliary tree has several branches, bifurcations, and/or adjoining lumens. Placement of a covered endoprosthesis or stent across a bifurcation and/or an opening of an adjacent branch or lumen to treat a stricture or blocked body lumen may result in additional blockage of a currently open or unrestricted lumen, which may be undesirable. There is an ongoing need to provide alternative endoprostheses or stents as well as alternative methods for manufacturing and using endoprostheses or stents.

SUMMARY

In a first example, an endoprosthesis may comprise: an expandable framework having a lumen extending from a first end of the expandable framework to a second end of the expandable framework. The expandable framework includes a body portion disposed between the first end and the second end. The expandable framework also includes a bowl portion disposed along the body portion between the first end and the second end. A polymeric cover is disposed on at least a portion of the expandable framework. The bowl portion extends radially outward from the body portion. An inner surface of the bowl portion and/or a portion of the body portion extending into an interior of the bowl portion is devoid of the polymeric cover to permit fluid to flow from the interior of the bowl portion through the expandable framework into the lumen at a location between the first end and the second end.

In addition or alternatively to any example disclosed herein, the polymeric cover includes a first portion extending from the first end toward the bowl portion and a second portion extending from the second end towards the bowl portion.

In addition or alternatively to any example disclosed herein, the second portion of the polymeric cover extends into the interior of the bowl portion.

In addition or alternatively to any example disclosed herein, the first portion of the polymeric cover extends along an outer surface of the bowl portion.

In addition or alternatively to any example disclosed herein, the first portion of the polymeric cover longitudinally overlaps the second portion of the polymeric cover.

In addition or alternatively to any example disclosed herein, the first portion is spaced apart radially outward from the second portion where the first portion of the polymeric cover longitudinally overlaps the second portion of the polymeric cover.

In addition or alternatively to any example disclosed herein, the bowl portion is integrally formed with the body portion.

In addition or alternatively to any example disclosed herein, the bowl portion includes an outer wall and an inner wall everted into the interior of the bowl portion from the outer wall.

In addition or alternatively to any example disclosed herein, the inner wall of the bowl portion is disposed radially outward of the body portion.

In addition or alternatively to any example disclosed herein, the bowl portion includes an outer circumferential rim spaced radially outward from the body portion.

In addition or alternatively to any example disclosed herein, the endoprosthesis includes at least one radiopaque marker disposed along the outer circumferential rim.

In addition or alternatively to any example disclosed herein, the bowl portion includes an open end facing toward the second end.

In another example, an endoprosthesis may comprise: an expandable framework including a body portion disposed between a first end and a second end, and a bowl portion disposed along the body portion; and a polymeric cover disposed on at least a portion of the expandable framework. The bowl portion may include an inner surface and an outer surface spaced apart radially outward from the inner surface. The bowl portion may extend radially outward from the body portion. The inner surface of the bowl portion may be devoid of the polymeric cover.

In addition or alternatively to any example disclosed herein, the polymeric cover includes a first portion and a second portion discontinuous with the first portion, the first portion extending from the first end toward the bowl portion and along the outer surface of the bowl portion, and the second portion extending from the second end towards the bowl portion and into an interior of the bowl portion.

In addition or alternatively to any example disclosed herein, the polymeric cover includes a first portion extending from the first end toward the bowl portion and a second portion extending from the second end towards the bowl portion.

In addition or alternatively to any example disclosed herein, the second portion of the polymeric cover extends into an interior of the bowl portion.

In addition or alternatively to any example disclosed herein, the first portion of the polymeric cover extends along the outer surface of the bowl portion.

In addition or alternatively to any example disclosed herein, the first portion of the polymeric cover longitudinally overlaps the second portion of the polymeric cover.

In addition or alternatively to any example disclosed herein, the first portion is spaced apart radially outward from the second portion where the first portion of the polymeric cover longitudinally overlaps the second portion of the polymeric cover.

In addition or alternatively to any example disclosed herein, the bowl portion is integrally formed with the body portion.

In addition or alternatively to any example disclosed herein, the polymeric cover is discontinuous.

In addition or alternatively to any example disclosed herein, the bowl portion includes an outer rim spaced radially outward from the body portion.

In addition or alternatively to any example disclosed herein, the endoprosthesis may include at least one radiopaque marker disposed along the outer rim.

In addition or alternatively to any example disclosed herein, the bowl portion includes an open end facing toward the second end.

In addition or alternatively to any example disclosed herein, an endoprosthesis may comprise: an expandable framework including a body portion disposed between a first end and a second end, a first flared portion proximate the first end and a second flared portion proximate the second end, and a bowl portion disposed between the first flared portion and the second flared portion; and a polymeric cover disposed on at least a portion of the expandable framework. The bowl portion may include an inner surface and an outer surface spaced apart radially outward from the inner surface. The bowl portion may extend radially outward from the body portion. The inner surface of the bowl portion may be devoid of the polymeric cover.

In addition or alternatively to any example disclosed herein, the inner surface of the bowl portion is disposed radially outward of the body portion.

In addition or alternatively to any example disclosed herein, the inner surface extends from an axial position adjacent a base of the bowl portion towards the second end.

In addition or alternatively to any example disclosed herein, a method of manufacturing an endoprosthesis may comprise:

wrapping one or more filaments onto a braiding mandrel to form an expandable framework;

shaping the expandable framework with a forming mandrel comprising a first forming portion and a second forming portion to form a first flared portion and a second flared portion opposite the first flared portion;

wherein the first forming portion has a first tubular body portion and a first enlarged end portion, and the second forming portion has a second tubular body portion and a second enlarged end portion;

disposing a forming collar over a body portion of the expandable framework between the first flared portion and the second flared portion;

translating the first forming portion and the forming collar axially relative to each other to urge a portion of the body portion of the expandable framework over an outer surface of the forming collar to form a bowl portion of the expandable framework; and heat treating the expandable framework to set the expandable framework in a deployed configuration.

In addition or alternatively to any example disclosed herein, after translating the first forming portion and the forming collar, the expandable framework extends continuously from the second flared portion towards the first flared portion within the forming collar, around a tip of the forming collar, from the tip of the forming collar towards the second flared portion along the outer surface of the forming collar to an outer rim of the bowl portion, and from the outer rim of the bowl portion towards the first flared portion.

In addition or alternatively to any example disclosed herein, the bowl portion of the expandable framework comprises an inner surface and an outer surface radially spaced apart from the inner surface.

In addition or alternatively to any example disclosed herein, the method may further comprise disposing a polymeric cover over at least a portion of the expandable framework.

In addition or alternatively to any example disclosed herein, a portion of the polymeric cover extends into an interior of the bowl portion of the expandable framework.

In addition or alternatively to any example disclosed herein, the inner surface of the bowl portion is devoid of the polymeric cover.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
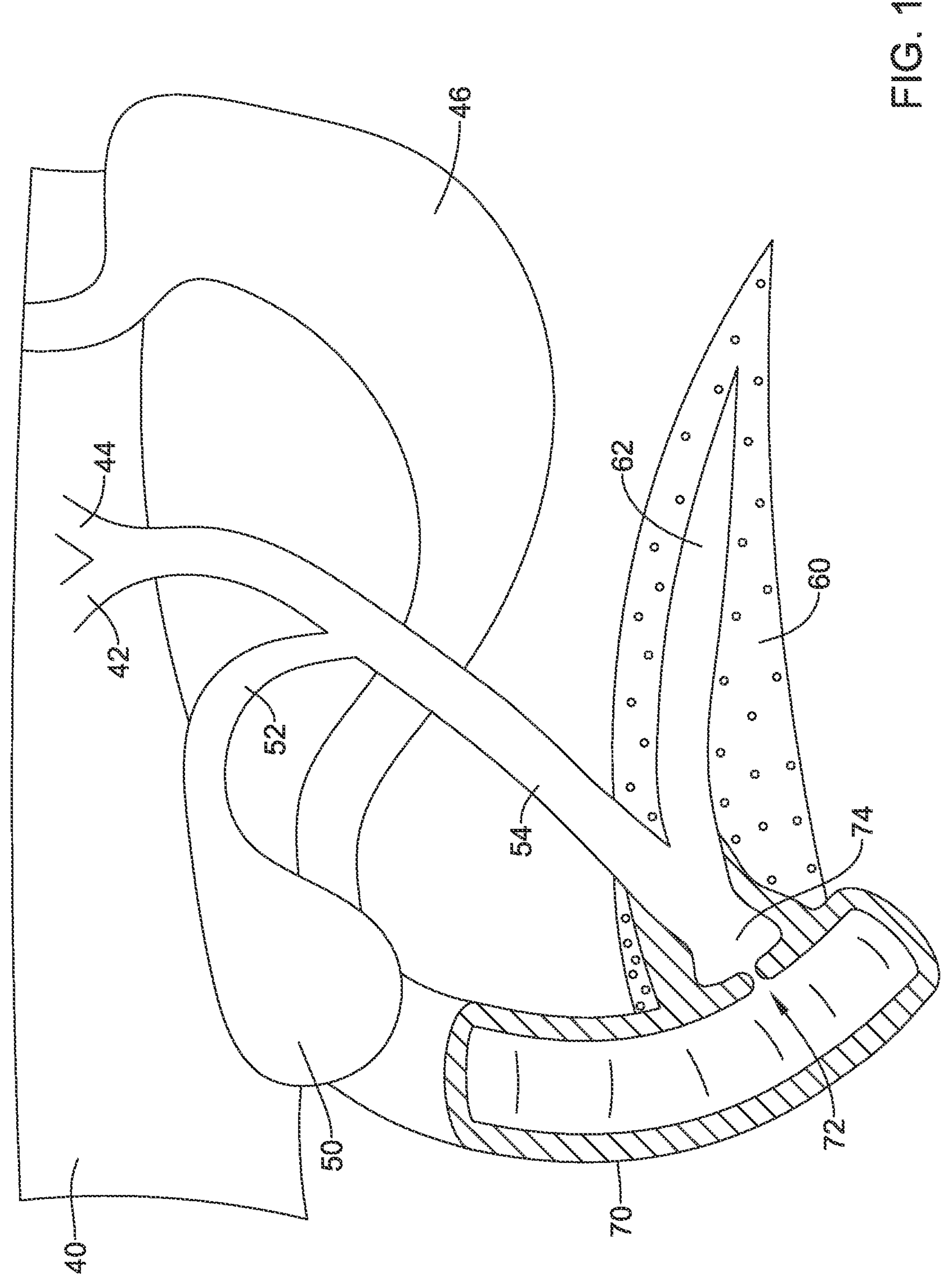
FIG. 1 illustrates aspects of a patient's biliary tree.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures illustrate selected components and/or arrangements of an endoprosthesis or stent. It should be noted that in any given figure, some features of the endoprosthesis or stent may not be shown, or may be shown schematically, for simplicity. Additional details regarding some of the components of the endoprosthesis or stent may be illustrated in other figures in greater detail. It is to be noted that in order to facilitate understanding, certain features of the disclosure may be described in the singular, even though those features may be plural or recurring within the disclosed embodiment (s). Each instance of the features may include and/or be encompassed by the singular disclosure(s), unless expressly stated to the contrary. For example, a reference to "the filament", "the cell", "the strut", or other features may be equally referred to all instances and quantities beyond one of said feature. As such, it will be understood that the following discussion may apply equally to any and/or all of the components for which there are more than one within the endoprosthesis or stent, unless explicitly stated to the contrary. Additionally, not all instances of some elements or features may be shown in each figure for clarity.

FIG. 1 illustrates selected features and relative positioning of a patient's anatomy related to the biliary tree, including the liver 40, the left hepatic duct 42, the right hepatic duct 44, the stomach 46, the gallbladder 50, the cystic duct 52, the common bile duct 54, the pancreas 60, the pancreatic duct 62, the duodenum 70 (shown partially cut away), the papilla of Vater 72, and the ampulla of Vater 74. In some patients, a stricture may form or develop that may partially or completely block a body lumen such as the common bile duct 54, the pancreatic duct 62, etc., thus requiring treatment. It will also be appreciated that this disclosure may be directed to features that facilitate and/or permit treatment of lumens the biliary tree while also maintaining drainage from branches and/or adjacent ducts into the lumen being treated.

Figure 2:
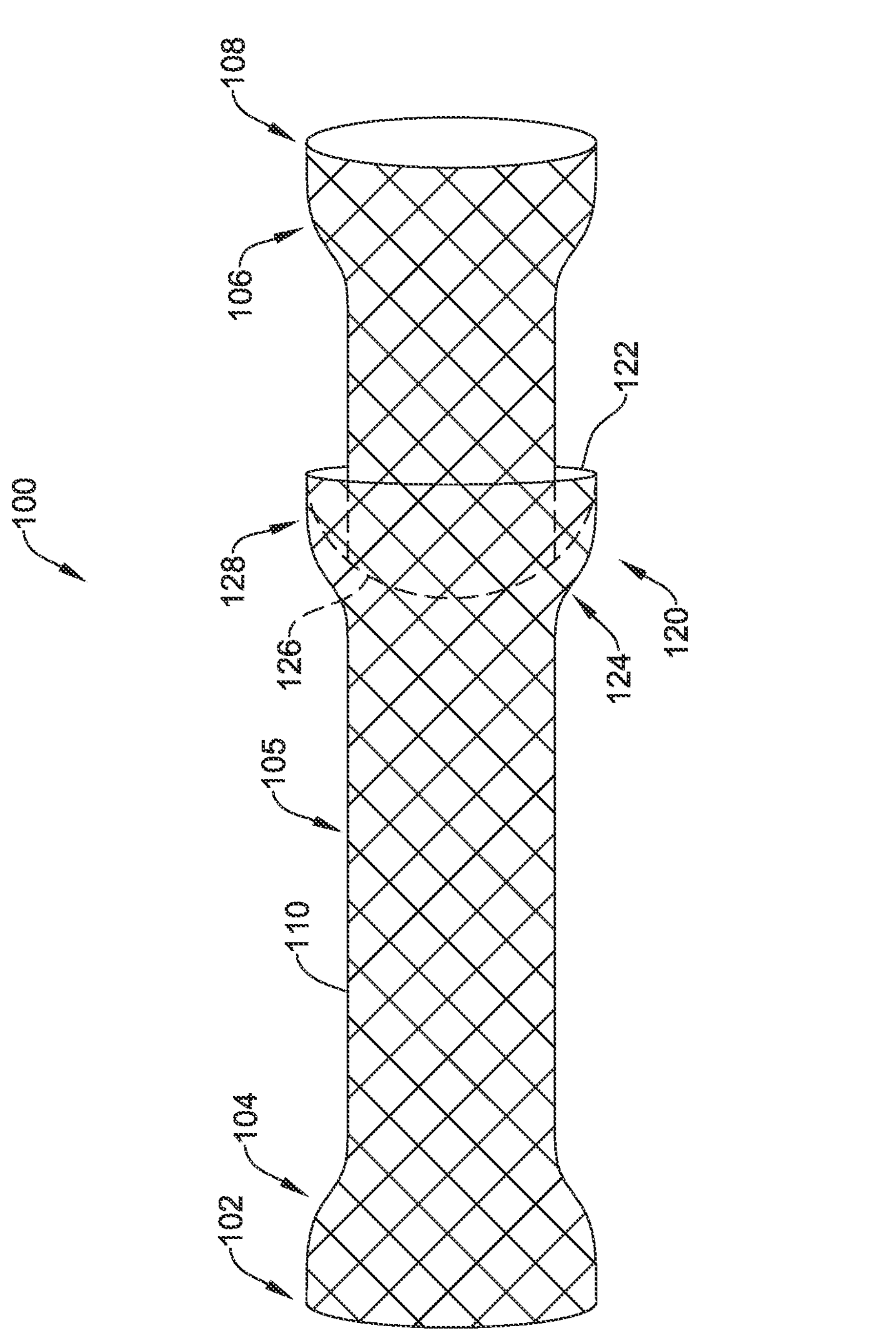
FIG. 2 is a side view illustrating aspects of an example endoprosthesis in a deployed configuration.
Figure 12:
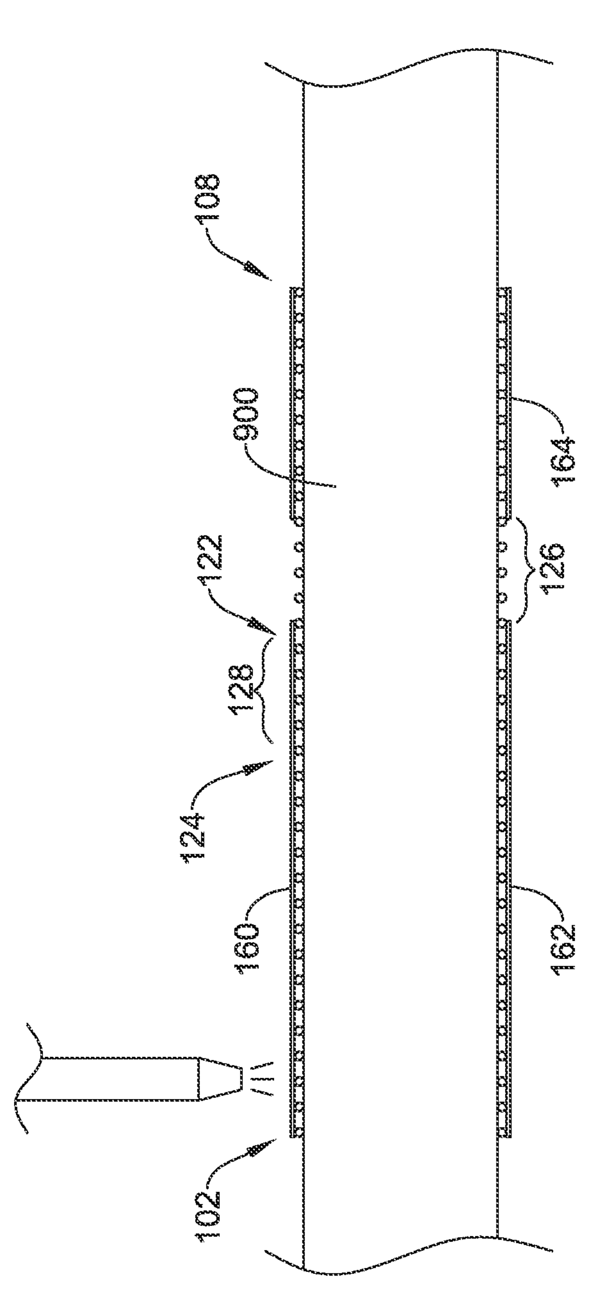

FIG. 2 illustrates an example endoprosthesis 100 (which term may be used interchangeably with the term "stent" herein) comprising an expandable framework 110 extending axially from a first end 102, which may be considered a proximal end in some instances, to a second end 108, which may be considered a distal end in some instances, along a central longitudinal axis of the endoprosthesis 100 and/or the expandable framework 110. The endoprosthesis 100 and/or the expandable framework 110 may be configured to shift between a radially contracted, delivery configuration (e.g., FIG. 5) and a radially expanded, deployed configuration (e.g., FIGS. 6-8). The delivery configuration may be a configuration in which the endoprosthesis 100 is axially elongated and/or radially collapsed or compressed compared to the deployed configuration. The deployed configuration may be a configuration in which the endoprosthesis 100 is axially shortened and/or radially expanded compared to the delivery configuration. In at least some embodiments, the endoprosthesis 100 and/or the expandable framework 110 may be self-expandable. For example, the endoprosthesis 100 and/or the expandable framework 110 may be formed from a shape memory material, such as nitinol. In some embodiments, the endoprosthesis 100 and/or the expandable framework 110 may be mechanically expandable. For example, the endoprosthesis 100 and/or the expandable framework 110 may be expandable using an inflatable balloon, using an actuation member, or other suitable means. During delivery to a treatment site, the endoprosthesis 100 and/or the expandable framework 110 may be disposed within a lumen of a delivery device in the delivery configuration. In the delivery confirmation, the endoprosthesis 100 may be axially elongated such that the inner wall of the bowl portion 120 (discussed herein) is not everted into the interior of the bowl portion 120, such as is shown in FIG. 12. Thus, when constrained within a delivery catheter or sheath, the expandable framework 110 is not everted on itself. Upon removal from the lumen of the delivery device, the endoprosthesis 100 and/or the expandable framework 110 may shift and/or may be shifted from the delivery configuration to the deployed configuration. For example, when deployed from the delivery catheter or sheath, the expandable framework 110 may evert upon itself to define the outer wall and the inner wall of the bowl portion 120 (discussed herein).

The expandable framework 110 may include and/or be formed with a plurality of cells. In some embodiments, the expandable framework 110 may include and/or be formed from one or more filaments interwoven around the central longitudinal axis of the endoprosthesis 100 and/or the expandable framework 110. In at least some embodiments, the one or more filaments may form and/or define the plurality of cells. In some embodiments, the expandable framework 110 may be braided, knitted, or woven from the one or more filaments. In some embodiments, the one or more filaments may be wires, threads, strands, etc. In some embodiments, adjacent filaments of the one or more filaments may define the cells (i.e., openings or interstices) through a wall of the expandable framework 110. Alternatively, in some embodiments, the expandable framework 110 may be a monolithic structure formed from a cylindrical tubular member, such as a single, cylindrical laser-cut nickel-titanium (e.g., Nitinol) tubular member, in which the remaining (e.g., unremoved) portions of the tubular member form the stent struts and/or framework with cells (i.e., openings or interstices) defined therebetween.

The expandable framework 110 may be substantially tubular and/or may include and/or define a lumen extending axially therethrough along the central longitudinal axis of the expandable framework 110 from the first end 102 to the second end 108. In some embodiments, the expandable framework 110 may have an axial length of about 40 millimeters to about 250 millimeters, about 50 millimeters to about 225 millimeters, about 60 millimeters to about 200 millimeters, about 80 millimeters to about 175 millimeters, about 100 millimeters to about 150 millimeters, or another suitable range. In some embodiments, the expandable framework 110 may have a radial outer dimension or radial extent of about 5 millimeters to about 30 millimeters, about 6 millimeters to about 25 millimeters, about 8 millimeters to about 20 millimeters, about 10 millimeters to about 15 millimeters, or another suitable range. Other configurations are also contemplated. Some suitable but non-limiting materials for the endoprosthesis 100, the expandable framework 110, and/or components or elements thereof, for example metallic materials and/or polymeric materials, are described below.

In at least some embodiments, the expandable framework 110 may be disposed within the body lumen extending through a stricture to maintain and/or re-establish patency of the body lumen. In some embodiments, the expandable framework 110 may be configured to dilate at least a portion of the body lumen in the deployed configuration. For example, expandable framework 110 may be configured to exert a radially outward force upon a wall of the body lumen (e.g., the common bile duct 54, the pancreatic duct 62, the duodenum 70, etc.) and/or against a stricture that has formed therein.

In some embodiments, the expandable framework 110 may include a first flared portion 104 proximate the first end 102 of the expandable framework 110. The first flared portion 104 may extend from the first end 102 toward the second end 108. In some embodiments, the expandable framework 110 may include a second flared portion 106 proximate the second end 108 of the expandable framework 110. The second flared portion 106 may extend from the second end 108 toward the first end 102. In at least some embodiments, the second flared portion 106 may be longitudinally and/or axially spaced apart from the first flared portion 104 by a body portion 105. In some embodiments, the body portion 105 may have a generally constant outer diameter along its length. In some embodiments, the first flared portion 104 may have a generally constant first outer diameter along its length. In some embodiments, the second flared portion 106 may have a generally constant second outer diameter along its length. Other configurations are also contemplated, including but not limited to, a constant taper along the first flared portion 104 and/or the second flared portion 106. In some embodiments, the first outer diameter may be greater than the outer diameter of the body portion 105. In some embodiments, the second outer diameter may be greater than the outer diameter of the body portion 105. In some embodiments, the first outer diameter may be substantially equal to the second outer diameter. In some embodiments, the first outer diameter may be different from the second outer diameter.

The expandable framework 110 may include a bowl portion 120 disposed along the body portion 105. The bowl portion 120 may fully circumferentially surround the body portion 105. In some embodiments, the bowl portion 120 may be integrally formed with the expandable framework 110 and/or the body portion 105. In some embodiments, the bowl portion 120 may be formed as a separate structure and later attached to the body portion 105. The bowl portion 120 may extend radially outward from the body portion 105 in the deployed configuration at a located between and spaced apart from the first flared portion 104 and the second flared portion 106. The bowl portion 120 may include an outer rim 122 extending around and spaced radially away from the body portion 105. Thus, the outer rim 122 may extending circumferentially around the entire circumference of the body portion 105. The outer rim 122 may define an outer diameter of the bowl portion 120 that is greater than the outer diameter of the body portion 105. In some embodiments, the outer diameter of the bowl portion 120 may be substantially equal to the first outer diameter and/or the second outer diameter. In some embodiments, the outer diameter of the bowl portion 120 may be greater than the outer diameter of the body portion 105, but less than the first outer diameter and/or the second outer diameter. In some embodiments, the outer diameter of the bowl portion 120 may be about 5% less, about 10% less, about 15% less, about 20% less, about 25% less, or another suitable amount less than the first outer diameter and/or the second outer diameter. In some embodiments, the outer diameter of the bowl portion 120 may be greater than the outer diameter of the body portion, and also greater than the first outer diameter and/or the second outer diameter. In some embodiments, the outer diameter of the bowl portion 120 may be about 5% greater, about 10% greater, about 15% greater, about 20% greater, about 25% greater, or another suitable amount greater than the first outer diameter and/or the second outer diameter.

The bowl portion 120 may include an outer rim 122 and a base 124. The bowl portion 120 may extend from the base 124 to the outer rim 122. The base 124 may be at the proximal most extent of the bowl portion 120 and the outer rim 122 may be at the distalmost extent of the bowl portion 120. The bowl portion 120 may be connected to and/or integrally formed with the body portion 105 at the base 124. In at least some embodiments, the outer rim 122 may define the outermost diameter of the bowl portion 120. The bowl portion 120 may include and/or define an axial depth extending from the outer rim 122 to the base 124 parallel to the central longitudinal axis of the endoprosthesis 100 and/or the expandable framework 110 in the deployed configuration. In some instances the axial depth may be between about 2-millimeters, between about 4-10 millimeters, between about 6-10 millimeters, between about 2-8 millimeters, or between about 2-5 millimeters, for example. In some instances the axial depth may be about 2 millimeters or more, about 5 millimeters or more, about 8 millimeters or more, or about 10 millimeters or more. In some instances the axial depth may be about 15 millimeters or less, about 10 millimeters or less, or about 5 millimeters or less. The bowl portion 120 may include an open end at the outer rim 122 extending into the interior of the bowl portion 120. The bowl portion 120 and/or the open end may face towards the second end 108 of the expandable framework 110. In other words, the rim 122 may be positioned closer to the second end 108 than the base 124. The bowl portion 120 may be formed from a portion of the body portion 105 of the expandable framework 110. For example, the bowl portion 120 may be formed by folding or everting a portion of the body portion 105 back on itself at the outer rim 122 and/or over itself adjacent the base 124. In doing so, the expandable framework 110 forms a double-walled portion for the bowl portion 120 including an inner wall having an inner surface 126, such as a concave inner surface, of the bowl portion 120 and an outer wall having an outer surface 128, such as a convex outer surface, of the bowl portion 120. The inner surface 126 of the bowl portion 120 (i.e., the inner surface 126 of the inner wall of the bowl portion 120) extends from the outer rim 122 of the bowl portion 120 towards the base 124 of the bowl portion 120 and/or the first end 102 of the expandable framework 110. The inner surface 126 of the bowl portion 120 may extend from an axial position adjacent the base 124 of the bowl portion 120 towards the second end 108. The outer surface 128 of the bowl portion 120 (i.e., the outer surface 128 of the outer wall of the bowl portion 120) extends from the outer rim 122 of the bowl portion 120 towards the base 124 of the bowl portion 120 and/or the first end 102 of the expandable framework 110. The outer surface 128 of the bowl portion 120 is disposed and/or spaced apart radially outward of the inner surface 126 of the bowl portion 120. Thus, the bowl portion 120 may be formed with a doubled over or everted portion of the wall of the expandable framework 110, in which a first wall portion, forming the inner surface 126, is positioned radially within a second wall portion, forming the outer surface 128.

Thus, both the outer wall forming the outer surface 126 and the inner wall forming the inner surface 126 of the bowl portion 120 may be formed by and include the interwoven filament(s) extending along the body portion 105 of the expandable framework 110. In other words, the interwoven filament(s) forming the expandable framework 110 may extend continuously through the body portion 105 proximal of the bowl portion 120, through the outer wall portion of the bowl portion 120, through the inner wall portion of the bowl portion 120, and through the body portion 105 distal of the bowl portion 120.

In some embodiments, the outer surface 128 of the bowl portion 120 may be tapered radially outward from the base 124 of the bowl portion 120 toward the second end 108 and/or the outer rim 122 of the bowl portion 120. In some embodiments, the outer surface 128 of the bowl portion 120 may be curved radially outward toward the second end 108 and/or the outer rim 122 of the bowl portion 120. In some embodiments, the outer surface 128 of the bowl portion 120 may be conically shaped, with the outer surface 128 extending radially outward toward the second end 108 and/or the outer rim 122 of the bowl portion 120. In some embodiments, the inner surface 126 of the bowl portion 120 may be tapered radially outward from an axial position adjacent the base 124 of the bowl portion 120 towards the second end 108 and/or the outer rim 122 of the bowl portion 120. In some embodiments, the inner surface 126 of the bowl portion 120 may be curved radially outward toward the second end 108 and/or the outer rim 122 of the bowl portion 120. In some embodiments, the inner surface 126 of the bowl portion 120 may be conically shaped, with the inner surface 126 extending radially outward toward the second end 108 and/or the outer rim 122 of the bowl portion 120. In some embodiments, the inner surface 126 and the outer surface 128 may have substantially the same shape and/or contour. In some embodiments, the inner surface 126 and the outer surface 128 may have different shapes and/or contours.

In some embodiments, the endoprosthesis 100, the first flared portion 104, the body portion 105, the second flared portion 106, and/or the bowl portion 120 may be configured to dilate at least a portion of the body lumen being treated in the deployed configuration. For example, the endoprosthesis 100, the first flared portion 104, the body portion 105, the second flared portion 106, and/or the bowl portion 120 may be configured to exert a radially outward force upon a wall of the body lumen being treated. In some embodiments, the body portion 105 may be configured to extend across an opening to an adjoining body lumen (e.g., a branch lumen, a papilla, etc.) and may be configured to exert less radially outward force on the opening of the adjoining body lumen than the first flared portion 104, the second flared portion 106, and/or the bowl portion 120 exerts on the body lumen being treated. In at least some embodiments, the first flared portion 104, the second flared portion 106, and/or the bowl portion 120 may be configured to exert the radially outward force upon the wall of the body lumen being treated to prevent migration of the endoprosthesis 100 within the body lumen.

Figure 3:
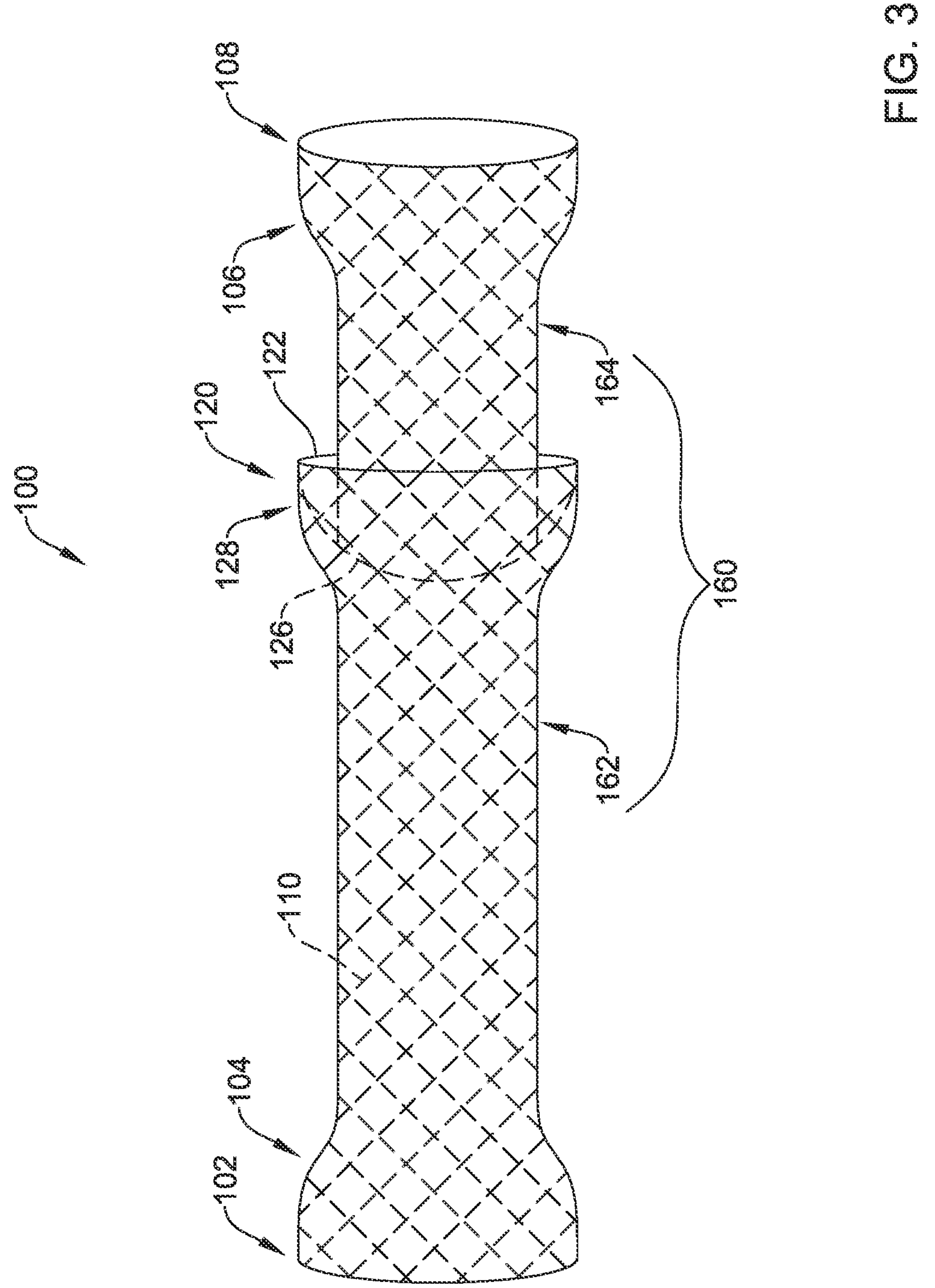
FIG. 3 is a side view illustrating aspects of the example endoprosthesis including a covering.

As seen in FIG. 3, the endoprosthesis 100 may include a polymeric cover 160 disposed on and/or over at least a portion of the expandable framework 110. In some embodiments, the polymeric cover 160 may be disposed on the first flared portion 104, the second flared portion 106, and/or the body portion 105 extending therebetween. In some embodiments, the polymeric cover 160 may be disposed on the outer surface 128 of the bowl portion 120. In some embodiments, the polymeric cover 160 may be disposed on and/or along an outer surface of the expandable framework 110. In some embodiments, the expandable framework 110 may be embedded in the polymeric cover 160. In some embodiments, the outer surface 128 of the bowl portion 120 may be embedded within the polymeric cover 160. In some embodiments, the polymeric cover 160 may be fixedly or releasably secured to, bonded to, or otherwise attached to the expandable framework 110 and/or the outer surface 128 of the bowl portion 120.

In some embodiments, the polymeric cover 160 may be impermeable to fluids, debris, medical instruments, etc. An interior of the bowl portion 120 and/or the inner surface 126 of the bowl portion 120, or at least a portion thereof, may be devoid of the polymeric cover 160. As such, the interior and/or the inner surface 126 of the bowl portion 120 may be configured to permit unobstructed passage of fluids, debris, medical instruments, etc. into the lumen of the endoprosthesis 100 and/or the expandable framework 110. For example, the inner surface 126 of the bowl portion 120 which is devoid of the polymeric cover 160 may include open cells defined between adjacent filaments of the expandable framework 110, permitting fluid to pass through the open cells into the lumen of the endoprosthesis 100. In some embodiments, the outer rim 122 of the bowl portion 120 may be at least partially defined by one or more edges of the polymeric cover 160. In some embodiments, the polymeric cover 160 may be coincident with and/or may align with the one or more filaments of the expandable framework 110 defining the outer rim 122 of the bowl portion 120. In some embodiments, the one or more edges of the polymeric cover 160 may terminate at the one or more filaments defining the outer rim 122 of the bowl portion 120. In at least some embodiments, the polymeric cover 160 disposed on the outer surface 128 of the bowl portion 120 may guide and/or direct fluids, debris, medical instruments, etc. into the lumen of the endoprosthesis 100 and/or the expandable framework 110 through the interior and/or the inner surface 126 of the bowl portion 120. Some suitable but non-limiting materials for the polymeric cover 160 are described below.

In some embodiments, the polymeric cover 160 may extend along an entire length of the endoprosthesis 100 and/or the expandable framework 110, except for the inner surface 126 of the inner wall of the bowl portion 120 and/or a portion of the body portion 105 located within the interior of the bowl portion 120 between the base 124 of the bowl portion 120 and the rim 122 of the bowl portion 120. In some embodiments, the polymeric cover 160 may extend along a portion of the length of the endoprosthesis 100 and/or the expandable framework 110. In some embodiments, the polymeric cover 160 may be discontinuous. In some embodiments, the polymeric cover 160 may extend discontinuously between the first end 102 (e.g., the proximal end) of the endoprosthesis 100 and/or the expandable framework 110 and the second end 108 (e.g., the distal end) of the endoprosthesis 100 and/or the expandable framework 110 in the deployed configuration. In some embodiments, the polymeric cover 160 may extend continuously from the first end 102 (e.g., the proximal end) of the endoprosthesis 100 and/or the expandable framework 110 to the second end 108 (e.g., the distal end) of the endoprosthesis 100 and/or the expandable framework 110 in the deployed configuration, except for the inner surface 126 of the inner wall of the bowl portion 120 and/or a portion of the body portion 105 located within the interior of the bowl portion 120 between the base 124 of the bowl portion 120 and the rim 122 of the bowl portion 120. In some embodiments, at least some cells of the plurality of cells (e.g., along the inner surface 126 of the inner wall of the bowl portion 120 and/or along a portion of the body portion 105 located within the interior of the bowl portion 120 between the base 124 of the bowl portion 120 and the rim 122 of the bowl portion 120) defined between adjacent filaments of the expandable framework 110 may be completely uncovered by the polymeric cover 160. Other configurations are also contemplated.

In some embodiments, the polymeric cover 160 may include a first portion 162 extending from the first end 102 and/or the first flared portion 104 toward and/or to the outer rim 122 of the bowl portion 120. In some embodiments, the first portion 162 of the polymeric cover 160 may extend on and/or along the outer surface 128 of the bowl portion 120 such as the outer surface 128 of the outer wall of the bowl portion 120. In some embodiments, the polymeric cover 160 may include a second portion 164 extending from the second end 108 and/or the second flared portion 106 toward and/or to the inner surface 126 of the inner wall of the bowl portion 120. In some embodiments, the second portion 164 of the polymeric cover 160 may extend into the interior of the bowl portion 120 to the inner surface 126 of the inner wall of the bowl portion 120. In some embodiments, the first portion 162 of the polymeric cover 160 may longitudinally and/or axially overlap the second portion 164 of the polymeric cover 160 in the deployed configuration. At locations where the first portion 162 of the polymeric cover 160 longitudinally and/or axially overlaps the second portion 164 of the polymeric cover 160 in the deployed configuration, the first portion 162 of the polymeric cover 160 may be radially spaced apart (e.g., spaced radially outward) from the second portion 164 of the polymeric cover 160 in the deployed configuration. The inner surface 126 of the inner wall of the bowl portion 120 may extend radially outward and/or toward the second end 108 from the second portion 164 of the polymeric cover 160. The inner wall of the bowl portion 120, such as the inner surface 126 of the inner wall of the bowl portion 120 may be devoid of the polymeric cover 160 and/or at least a portion of the body portion 105 that is overlapped by the bowl portion 120 may be devoid of the polymeric cover 160 such that open cells of the expandable framework 110 between the interwoven filament(s) allow fluid to flow therethrough into the lumen of the endoprosthesis 100.

Figure 3A:
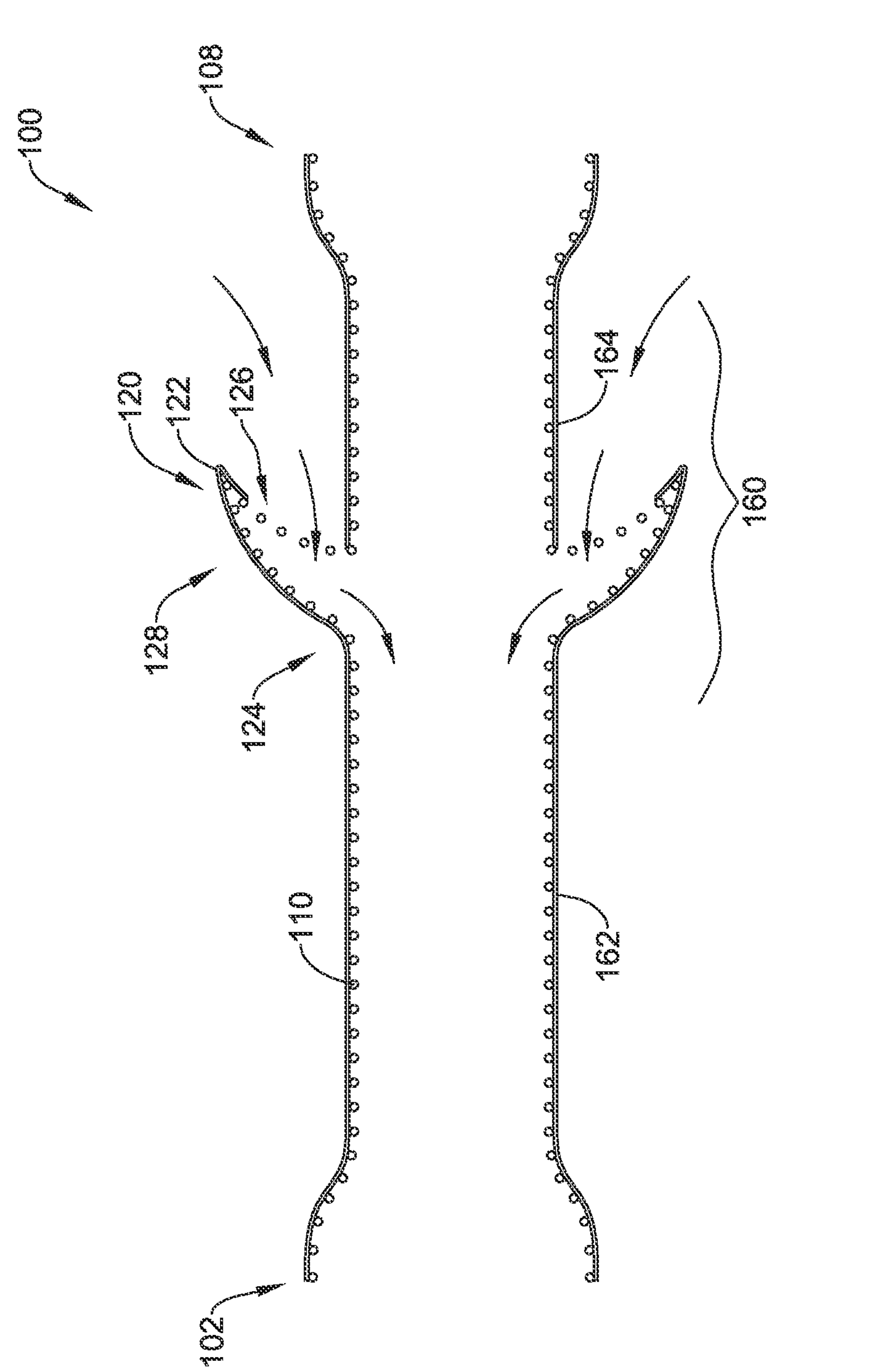
FIG. 3A is a longitudinal cross-sectional view of the example endoprosthesis of FIG. 3.

FIG. 3A illustrates the first portion 162 of the polymeric cover 160 extending on and/or along the outer surface 128 of the outer wall of the bowl portion 120 and the second portion 164 of the polymeric cover 160 extending on and/or along the outer surface of the body portion 105 into the interior of the bowl portion 120, while the inner surface 126 of the inner wall of the bowl portion 120, (e.g., the entire inner surface 126 or a portion thereof), is devoid of the polymeric cover 160 such that the cells defined between filaments of the expandable framework 110 are open along the inner surface 126 to permit fluid to flow from the interior of the bowl portion 120 into the central lumen of the endoprosthesis 100.

Figure 3B:
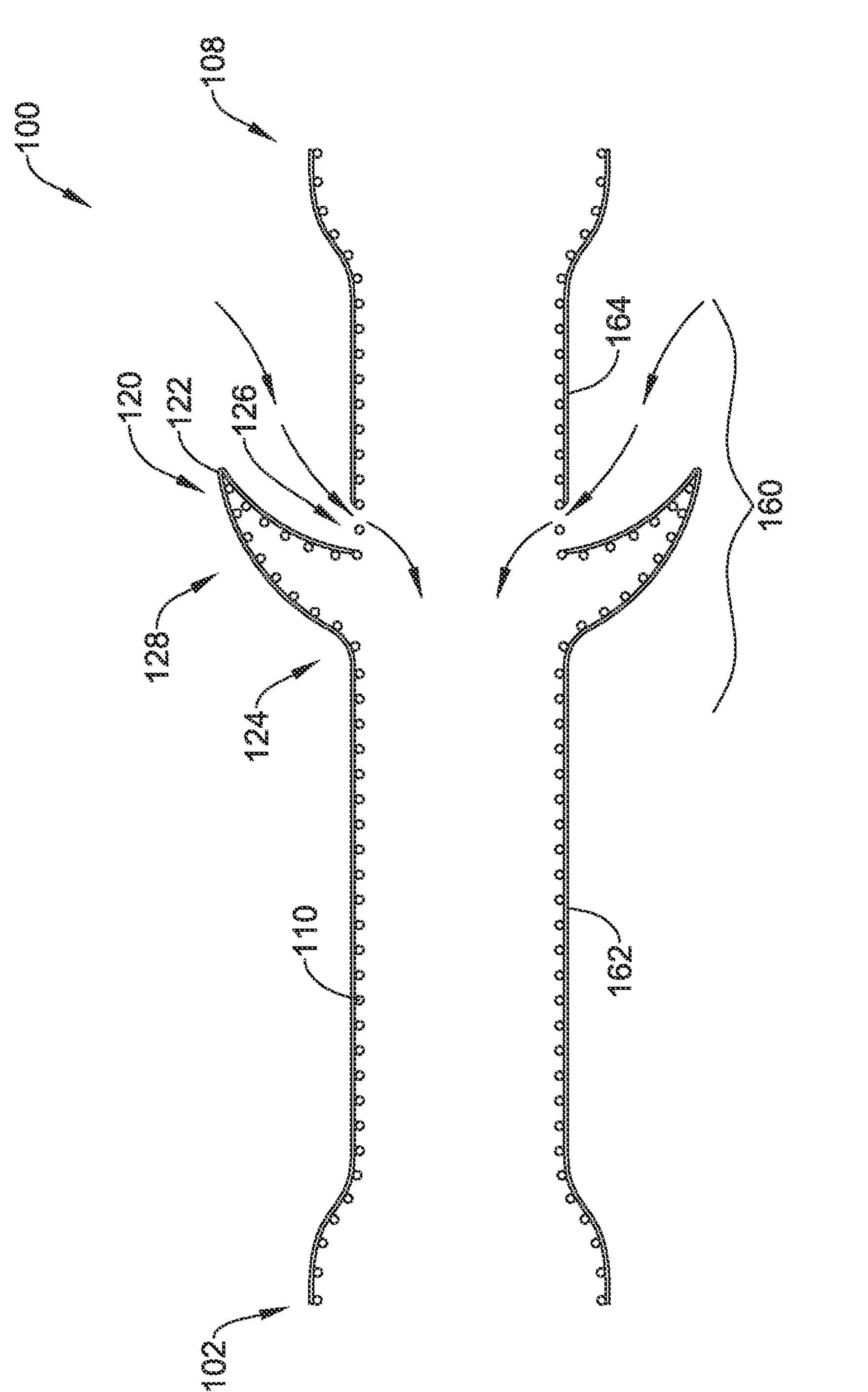
FIG. 3B is an alternative longitudinal cross-sectional view of the example endoprosthesis of FIG. 3.

FIG. 3B illustrates the first portion 162 of the polymeric cover 160 extending on and/or along the outer surface 128 of the outer wall of the bowl portion 120 and the inner surface 126 of the inner wall of the bowl portion 120, while the second portion 164 of the polymeric cover 160 extends on and/or along the outer surface of the body portion 105 into the interior of the bowl portion 120, while a portion of the body portion 105 located longitudinal between the base 124 and the rim 122 is devoid of the polymeric cover 160 such that the cells defined between filaments of the expandable framework 110 are open along the uncovered portion of the body portion 120 to permit fluid to flow from the interior of the bowl portion 120 into the central lumen of the endoprosthesis 100.

Figure 3C:
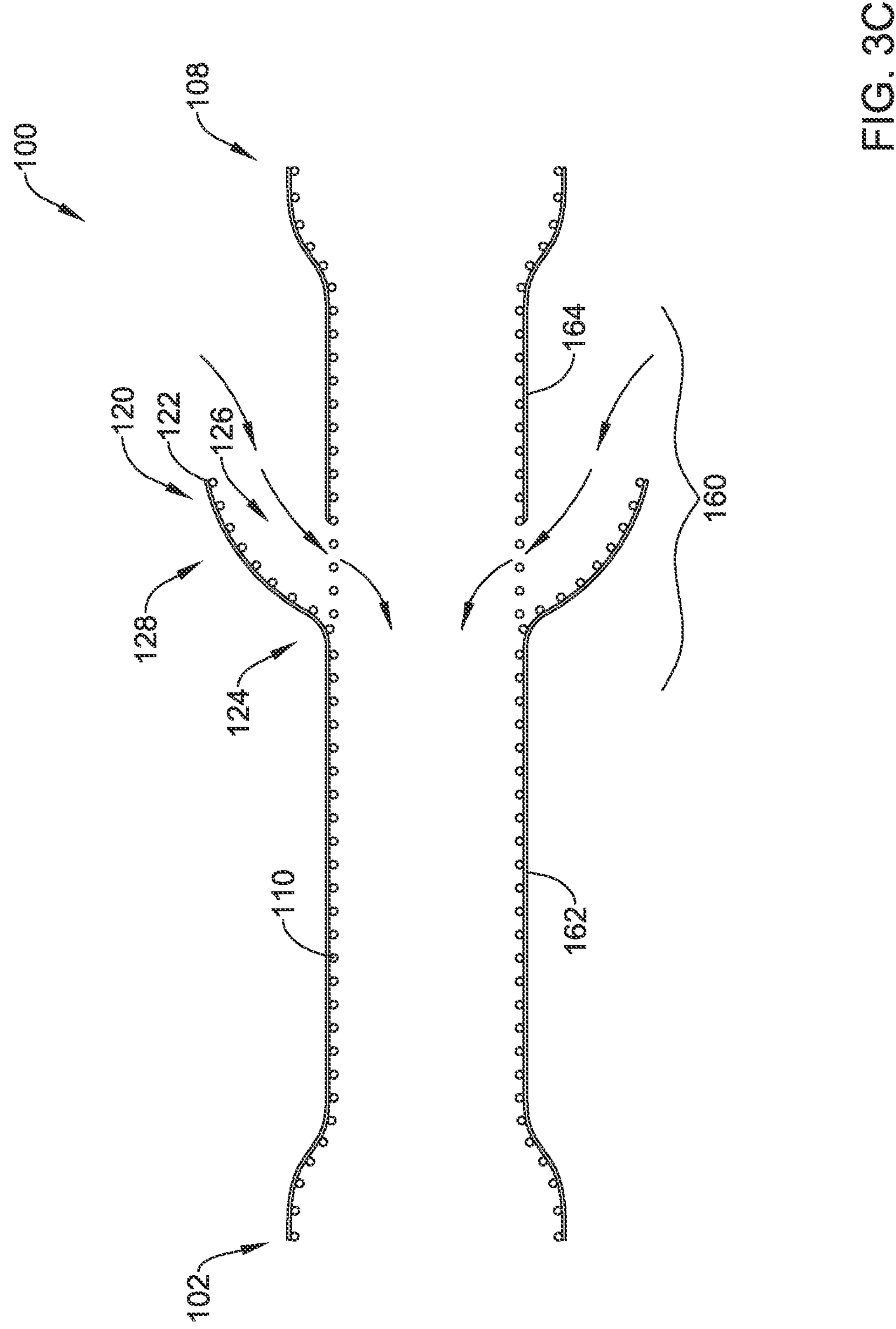
FIG. 3C is an alternative longitudinal cross-sectional view of a variation of the example endoprosthesis of FIG. 3.

FIG. 3C illustrates an alternative configuration in which the first portion 162 of the polymeric cover 160 extends on and/or along the body portion 105 proximal of the bowl portion 105 and the outer surface 128 of the wall of the bowl portion 120, while the second portion 164 of the polymeric cover 160 extends on and/or along the outer surface of the body portion 105 into the interior of the bowl portion 120, while a portion of the body portion 105 located longitudinal between the base 124 and the rim 122 is devoid of the polymeric cover 160 such that the cells defined between filaments of the expandable framework 110 are open along the uncovered portion of the body portion 120 to permit fluid to flow from the interior of the bowl portion 120 into the central lumen of the endoprosthesis 100.

Figure 4:
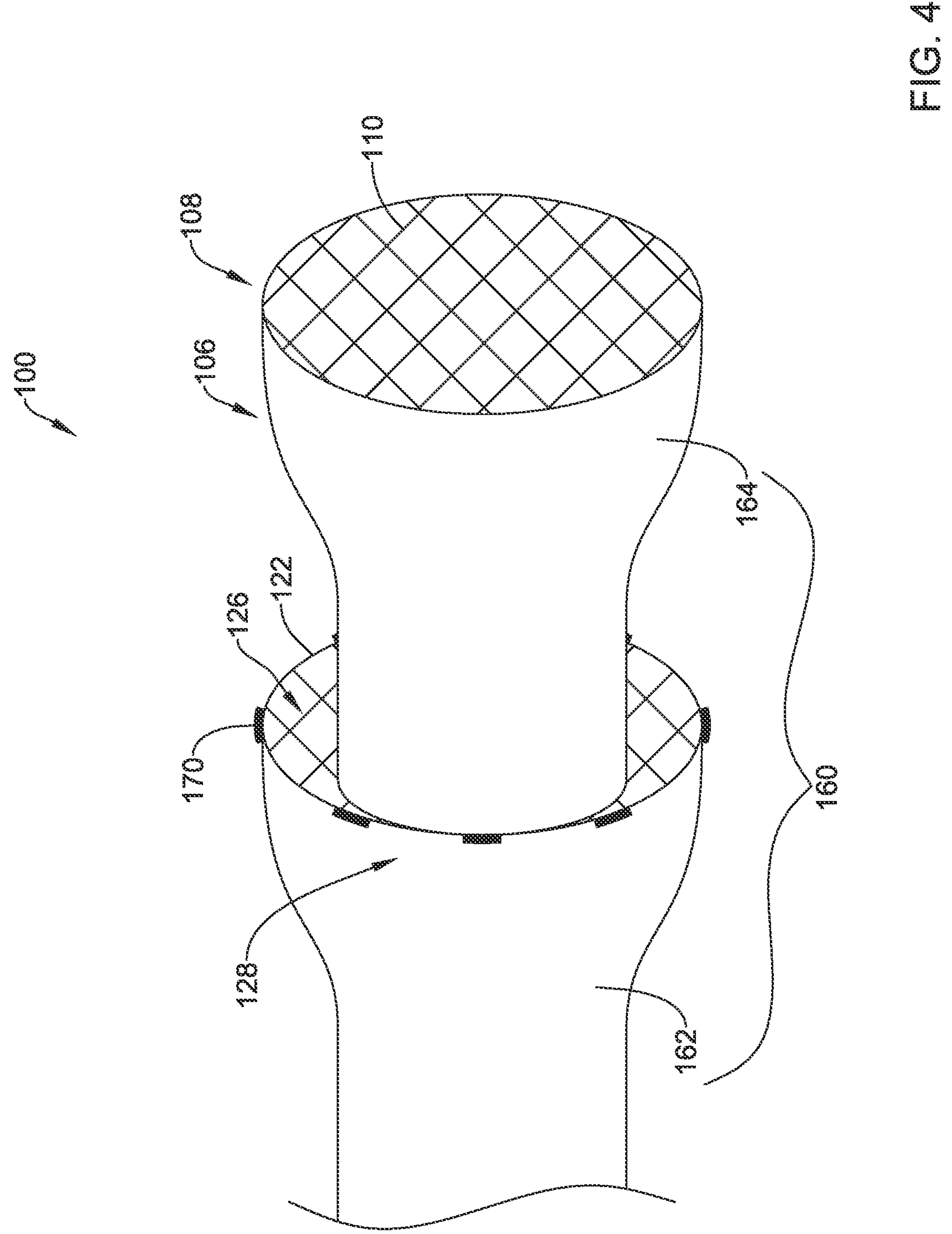
FIG. 4 is an angled view illustrating aspects of the example endoprosthesis.

To aid in positioning the endoprosthesis 100 within a body lumen, the endoprosthesis 100 may include at least one radiopaque marker 170 disposed at, on, and/or along the outer rim 122 of the bowl portion 120, as shown in FIG. 4. Some suitable but non-limiting materials for the at least one radiopaque marker 170 are described below.

In use, when the endoprosthesis 100 is positioned within a body lumen with the endoprosthesis 100 and/or the expandable framework 110 in the deployed configuration, the polymeric cover 160 disposed on and/or over the expandable framework 110 may form a barrier, such as a sealed interface, between the lumen of the endoprosthesis 100 and/or the expandable framework 110 and the wall of the body lumen positioned radially outward of the polymeric cover 160. The polymeric cover 160 may isolate the lumen of the endoprosthesis 100 and/or the expandable framework 110 from the wall of the body lumen. The polymeric cover 160 may prevent tissue ingrowth into the lumen and/or the expandable framework 110 of the endoprosthesis 100 and thereby permit and/or aid removal of the endoprosthesis 100 and/or the expandable framework 110 from the body lumen.

In some alternative embodiments and/or uses, implantation of the endoprosthesis 100 may be permanent and/or may not be intended to be removed. In some such embodiments and/or uses, the first flared portion 104 and/or the second flared portion 106 may be devoid of the polymeric cover 160 so as to promote tissue ingrowth at the first flared portion 104 and/or the second flared portion 106 and thereby prevent migration of the endoprosthesis 100 within the body lumen, while the body portion 105 and/or the bowl portion 120 retain and/or include the polymeric cover 160 to isolate the lumen of the endoprosthesis 100 from the wall of the body lumen and/or to prevent tissue ingrowth along the body portion 105 and/or the bowl portion 120 to maintain patency of the body lumen.

Figure 5:
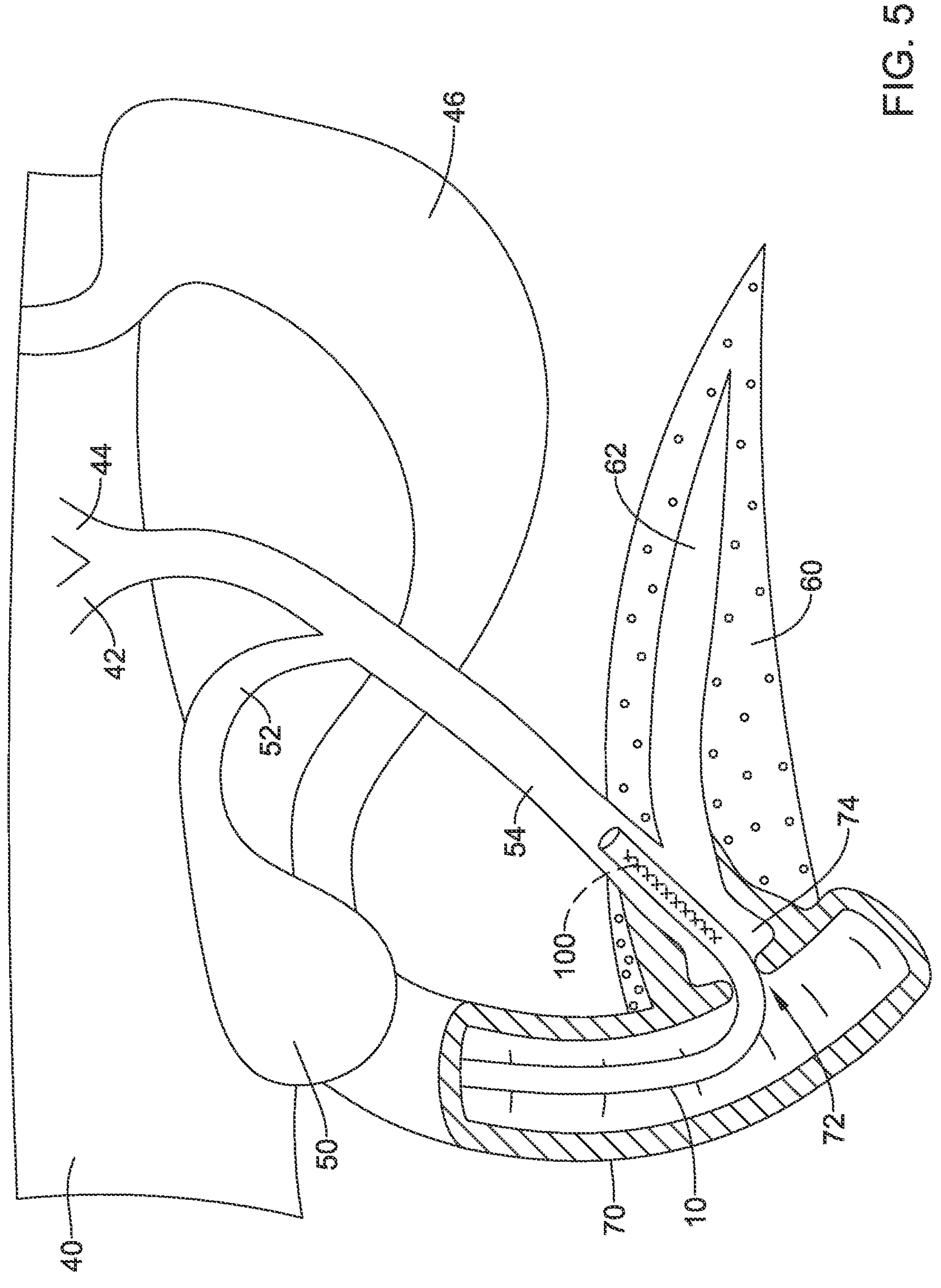
FIG. 5 illustrates aspects of delivering the example endoprosthesis to a body lumen.

FIG. 5 illustrates selected aspects of delivering the endoprosthesis 100 to a body lumen using a delivery device 10. In some embodiments, the delivery device 10 may be an elongate catheter or other tubular shaft suitable for and/or known in the art for delivering endoprostheses. The endoprosthesis 100 may be disposed within a lumen of the delivery device 10 in the delivery configuration (e.g., the endoprosthesis 100 is axially elongated and/or radially collapsed or compressed). In the delivery configuration, the bowl portion 120 may be unfolded and/or axially straightened such that the portion of the body portion 105 used to form the bowl portion 120 is no longer folded back on itself. In the delivery configuration, the expandable framework 110 may be substantially straight and/or fully elongated. The endoprosthesis 100 may be deployed from the delivery device 10 using one or more known techniques which are not described in the interest of brevity.

Figure 6:
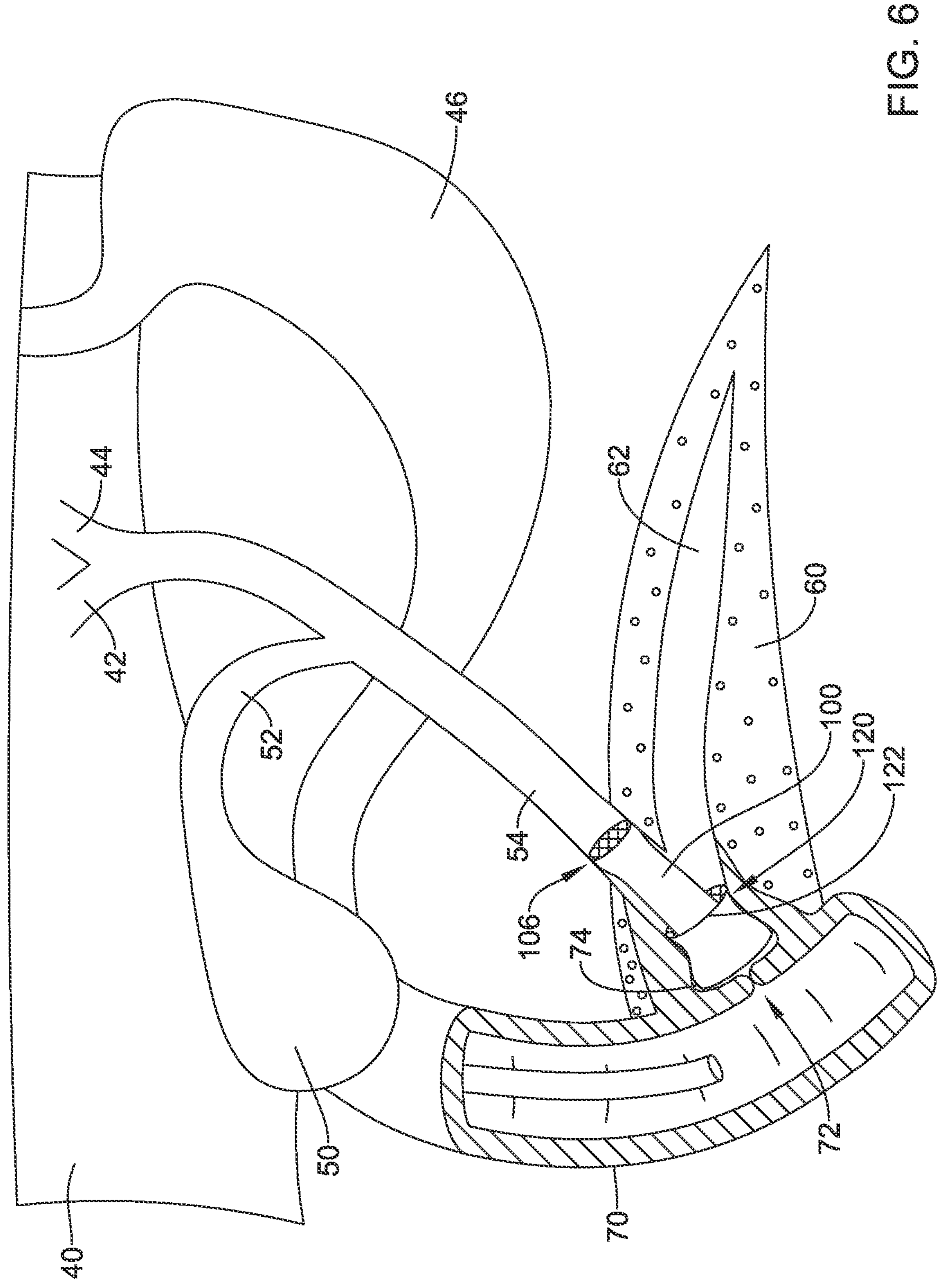
FIGS. 6-8 illustrates aspects of the example endoprosthesis deployed in various body lumens.
Figure 7:
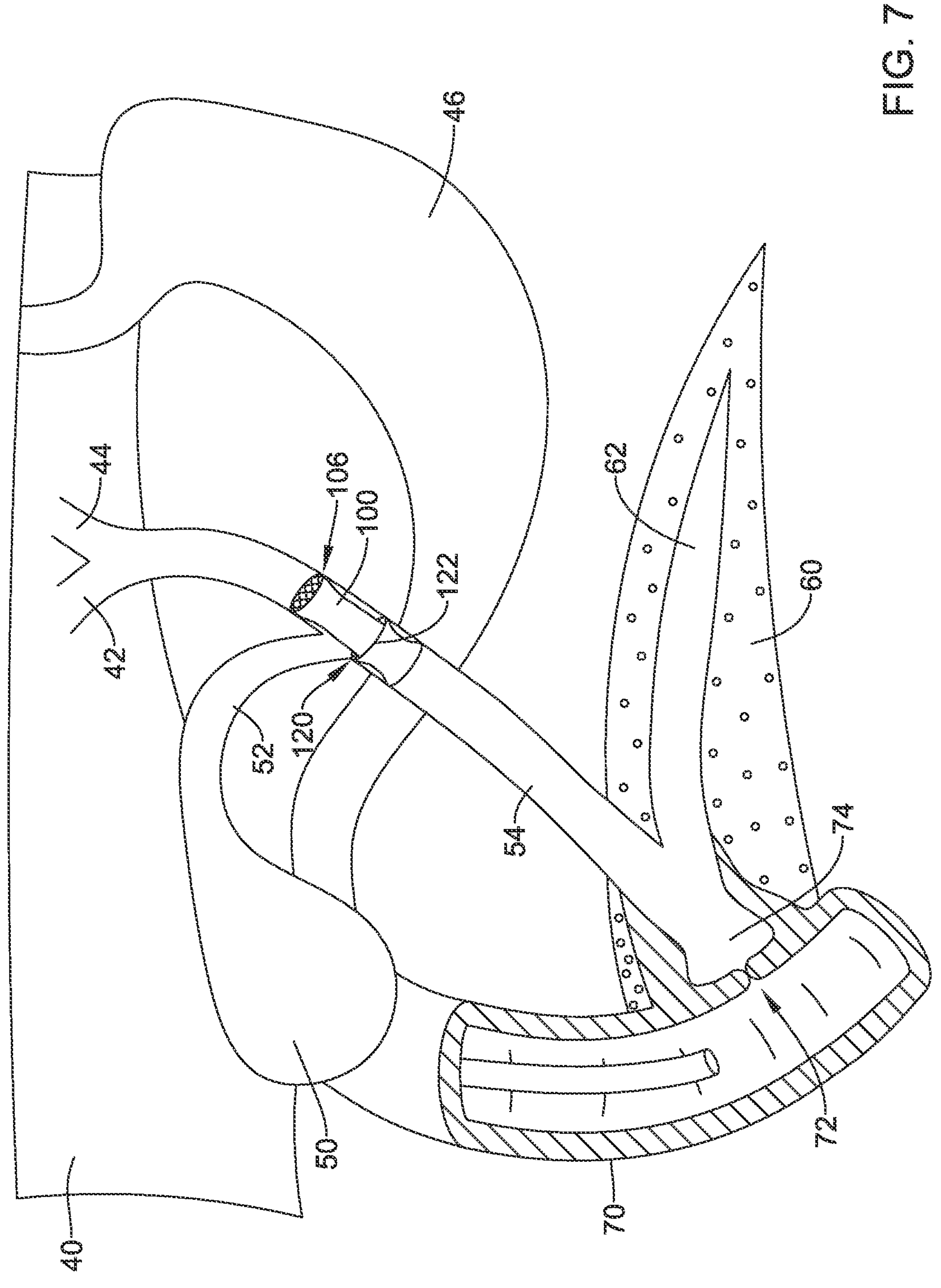
Figure 8:
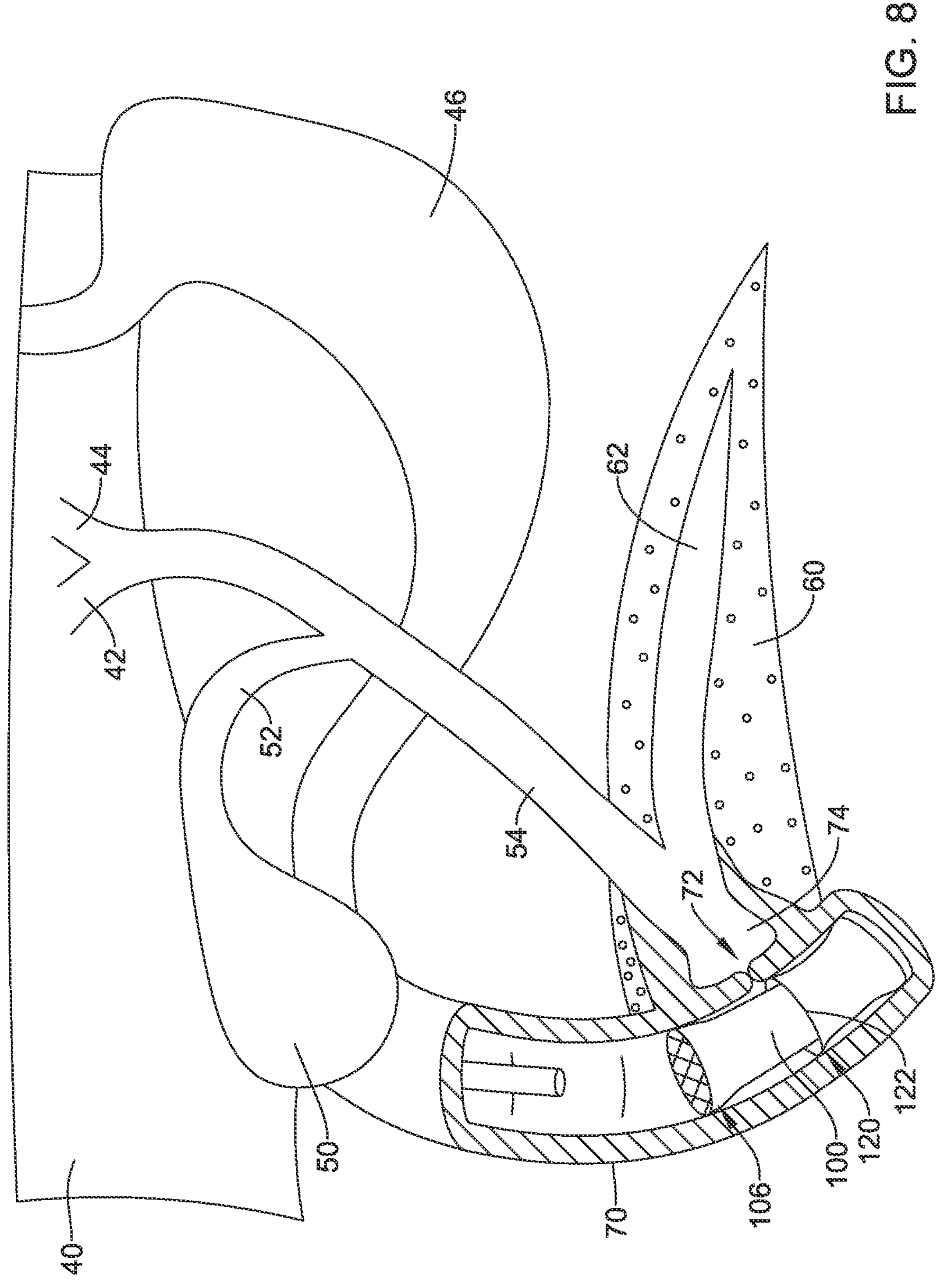

The endoprosthesis 100 may be positioned using a suitable imaging technique or other means such that the outer rim 122 of the bowl portion 120 is disposed downstream of and/or adjacent to an opening of an adjacent and/or branching body lumen by locating the at least one radiopaque marker 170 at the desired location. Upon deployment from the delivery device 10, the bowl portion 120 may re-form and/or reconstitute itself by folding the body portion 105 back on itself to shift from the delivery configuration to the deployed configuration of the endoprosthesis 100 described herein. In some embodiments, the bowl portion 120 may be disposed about 5 millimeters downstream of the opening of the adjacent and/or branching body lumen. In some embodiments, the bowl portion 120 may be disposed about 10 millimeters downstream of the opening of the adjacent and/or branching body lumen. In some embodiments, the bowl portion 120 may be disposed about 15 millimeters downstream of the opening of the adjacent and/or branching body lumen. In some embodiments, the bowl portion 120 may be disposed about 20 millimeters downstream of the opening of the adjacent and/or branching body lumen. In some embodiments, the bowl portion 120 may be disposed about 25 millimeters downstream of the opening of the adjacent and/or branching body lumen. In some embodiments, the bowl portion 120 may be disposed about 10 to about 15 millimeters downstream of the opening of the adjacent and/or branching body lumen. Other configurations and/or placements are also contemplated. FIGS. 6-8 illustrate the endoprosthesis 100 disposed within various body lumens and/or adjacent to branching body lumens. As may be appreciated, the configuration(s) of the endoprosthesis 100 disclosed herein may be beneficial when treating an adjacent and/or intersecting lumen, duct, and/or papilla.

In one example illustrated in FIG. 6, the second flared portion 106 extends into the common bile duct 54 and the outer rim 122 of the bowl portion 120 is disposed immediately downstream of the opening of the pancreatic duct 62. This positioning permits fluid and/or debris within the common bile duct 54 to flow through the lumen of the endoprosthesis 100 from the second end 108 of the endoprosthesis 100 while permitting fluid and/or debris within the pancreatic duct 62 to flow into the lumen of the endoprosthesis 100 through the interior of the bowl portion 120 without obstructing the pancreatic duct 62. Similarly, the same endoprosthesis 100 may be positioned with the second flared portion 106 extending within the pancreatic duct 62 and the outer rim 122 of the bowl portion 120 is disposed immediately downstream of the opening of the common bile duct 54. This positioning permits fluid and/or debris within the pancreatic duct 62 to flow through the lumen of the endoprosthesis 100 from the second end 108 of the endoprosthesis 100 while permitting fluid and/or debris within the common bile duct 54 to flow into the lumen of the endoprosthesis 100 through the interior of the bowl portion 120 without obstructing the common bile duct 54. Accordingly, in both examples, fluids and/or debris from both body lumens may flow through the lumen of the endoprosthesis 100 and/or the through the papilla of Vater 72 and into the duodenum 70.

In an alternative example illustrated in FIG. 7, the second flared portion 106 extends within the common bile duct 54 past the cystic duct 52 and toward the left hepatic duct 42 and the right hepatic duct 44, and the outer rim 122 of the bowl portion 120 is disposed immediately downstream of the opening of the cystic duct 52. This positioning permits fluid and/or debris within the common bile duct 54 to flow through the lumen of the endoprosthesis 100 from the second end 108 of the endoprosthesis 100 while permitting fluid and/or debris within the cystic duct 52 to flow into the lumen of the endoprosthesis 100 through the interior of the bowl portion 120 without obstructing the cystic duct 52. Similarly, the same endoprosthesis 100 may be positioned with the second flared portion 106 extending within the cystic duct 52 and the outer rim 122 of the bowl portion 120 is disposed immediately downstream of the opening of the cystic duct 52 into the common bile duct 54. This positioning permits fluid and/or debris within the cystic duct 52 to flow through the lumen of the endoprosthesis 100 from the second end 108 of the endoprosthesis while permitting fluid and/or debris within the common bile duct 54 and/or the left and right hepatic ducts 42/44 to flow into the lumen of the endoprosthesis 100 through the interior of the bowl portion 120 without obstructing the common bile duct 54 and/or the left and right hepatic ducts 42/44. Accordingly, in both examples, fluids and/or debris from both body lumens may flow through the lumen of the endoprosthesis 100 toward the papilla of Vater 72.

FIG. 8 illustrates one example configuration of the endoprosthesis 100 disposed within the duodenum 70 adjacent to the papilla of Vater 72. In some embodiments, the endoprosthesis 100 may be placed within the duodenum 70 of the patient endoscopically, surgically, or using other suitable means. The endoprosthesis 100 may be located using an appropriate imaging technique to place the outer rim 122 of the bowl portion 120 immediately downstream of the papilla of Vater 72. This positioning permits fluid and/or debris within the duodenum 70 to flow through the lumen of the endoprosthesis 100 from the second end 108 of the endoprosthesis 100 while permitting fluid and/or debris within the ampulla of Vater 74 to flow into the lumen of the endoprosthesis 100 through the interior of the bowl portion 120 without obstructing the papilla of Vater 72.

While not expressly illustrated, in some embodiments, the endoprosthesis 100 may include a semi-circular bowl wherein a portion or one side of the bowl portion 120 may be filled in with a polymeric material (e.g., silicone, etc.). Such a configuration may be beneficial or useful in situations where a stricture or lesion has formed in a main body lumen opposite a branch lumen or papilla. Fluid and/or debris within the main body lumen would be able to flow through the lumen of the endoprosthesis. The branch lumen or papilla would still be able to drain into the lumen of the endoprosthesis 100 while covering and/or protecting the stricture or lesion in the main body lumen. Alternatively, the bowl portion 120 could be formed with a semi-circular shape during manufacturing such that the bowl portion 120 assumes the semi-circular shape in the deployed configuration. In yet another alternative configuration, a portion or one side of the bowl portion 120 could be filled in with the polymeric material after the endoprosthesis 100 is deployed within the main body lumen.

In some embodiments, the bowl portion 120 and/or the inner surface 126 of the bowl portion 120 may be utilized to extend a medical device into the branch lumen or papilla. A second delivery device may be advanced within the lumen of the endoprosthesis 100, through the inner surface 126 and/or the bowl portion 120, and into the branch lumen or papilla, where the medical device may be deployed and/or used to effect treatment. The medical device may be a treatment catheter, a secondary stent, a balloon, or other medical device. In some embodiments, the endoprosthesis 100 may be suitable for and/or may be used as a portion of a stent system deployed at a bifurcation.

Figure 9:
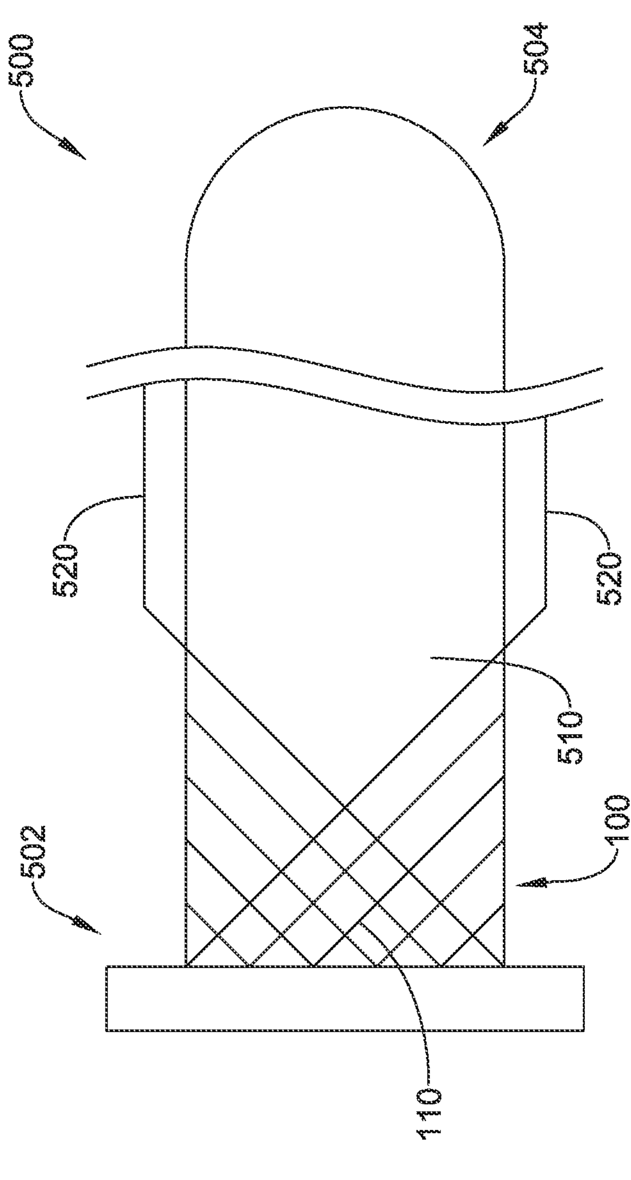
FIGS. 9-12 illustrates aspects of a method of making the example endoprosthesis.

FIG. 9 illustrates aspects of an example braiding mandrel 500 for use in manufacturing the expandable framework 110 of the endoprosthesis 100. The braiding mandrel 500 is a tubular cylindrical member having a distal end 504, a proximal end 502 configured to be secured to a braiding machine, and a longitudinal portion 510 extending between the proximal end 502 and the distal end 504. One or more filaments 520 may be wrapped, braided, and/or woven around the braiding mandrel 500 to form the expandable framework 110 of the endoprosthesis 100. In some embodiments, the one or more filaments 520 may include one filament, two filaments, three filaments, four filaments, five filaments, or additional filaments interwoven together as desired.

In some embodiments, the braiding mandrel 500 may include a plurality of securement projections disposed proximate the proximal end 502 and/or the distal end 504 useful for engaging the one or more filaments of the endoprosthesis 100 prior to commencement of braiding. In some embodiments, the plurality of securement projections may be formed as raised tabs. In some embodiments, the plurality of securement projections may have a rounded face for ease of securement of the one or more filaments and for safety by generally eliminating shaped and pointed faces on the braiding mandrel 500. In some embodiments, the plurality of securement projections may be useful for bending the one or more filaments about an under portion of the raised tab. In some embodiments, the under portion of the plurality of securement projections may be recessed from the rounded face to secure the one or more filaments thereat. In some embodiments, two or more of the one or more filaments may be secured to one and/or each of the plurality of securement projections.

The one or more filaments 520 may be wrapped, braided, and/or woven in a one-over and one-under pattern to form the endoprosthesis 100 via sinusoidal movement of the carriers of a braiding machine. Other configurations, including but not limited to a two-over and two-under pattern, are also contemplated. The one or more filaments 520 may non-interlockingly engage one another (e.g., cross over and/or cross under one another) in the braided pattern. Such a non-interlocking braided pattern may exclude, if desired, inter-twisting, inter-looping, inter-engaging and the like at intersections and/or crossings of the one or more filaments 520.

The longitudinal portion 510 may include a first plurality of raised projections. In some embodiments, the first plurality of raised projections may be arranged in a regular pattern over the longitudinal portion 510 of the braiding mandrel 500 such that adjacent or juxtaposed raised projections form guides or channels therebetween for receiving the one or more filaments 520 during braiding with the raised projections occupying the open cells between adjacent filaments 520. In at least some embodiments, the first plurality of raised projections may be pyramidally-shaped and/or formed like pyramids having a square or rectangular base and four triangular sides extending radially outward from a central longitudinal axis of the braiding mandrel 500. In some embodiments, the first plurality of raised projections many include truncated and/or rounded top portions. Other shapes and/or configurations are also contemplated. The first plurality of raised projections may be configured and arranged to form guides for receiving the one or more filaments 520 during braiding. In some embodiments, at least a part of the longitudinal portion 510 may be free or partially free of the first plurality of raised projections, depending on the characteristics of the endoprosthesis 100 to be produced. For example, the first plurality of raised projections need not necessarily be present along the whole braiding length and/or circumference of the longitudinal portion 510 of the braiding mandrel 500.

The braiding mandrel 500 may optionally include a proximal portion proximate the proximal end 502 and/or a distal portion proximate the distal end 504, wherein the proximal portion and/or the distal portion has a larger outer extent and/or diameter than the longitudinal portion 510 to thereby form the flared ends of the endoprosthesis 100. In some embodiments, the proximal portion and/or the distal portion may be omitted from the braiding mandrel 500. In some embodiments, there may be a tapered transition between the outer extent and/or diameter of the longitudinal portion 510 and the outer extent and/or diameter of the proximal portion and/or the distal portion. In some embodiments, the proximal portion and/or the distal portion may include a second plurality of raised projections, similar in form and function to the first plurality of raised projections. In some embodiments, the proximal portion and/or the distal portion may be configured to form the first flared portion 104 and/or the second flared portion 106, respectively. Other shapes and/or configurations of the braiding mandrel 500 are also contemplated. One example of a braiding mandrel and associated method of braiding an endoprosthesis is described in U.S. Pat. No. 8,151,682, the contents of which are incorporated herein by reference.

Figure 10:
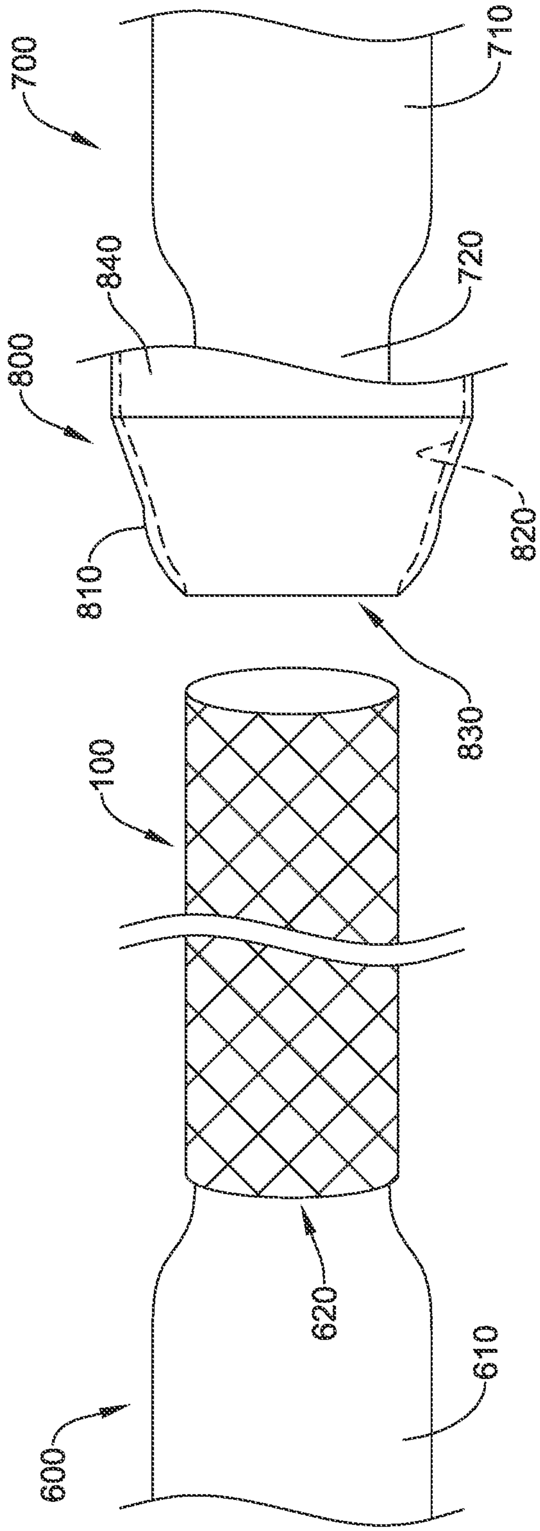

After forming the expandable framework 110 of the endoprosthesis 100 on the braiding mandrel 500, additional operations may be performed on the endoprosthesis 100. In some embodiments, the method may include shaping the expandable framework 110 with a forming mandrel comprising a first forming portion 600 and a second forming portion 700, as seen in FIG. 10. The first forming portion 600 may be configured to form the first flared portion 104 and/or to define and/or support the body portion 105. The second forming portion 700 may be configured to form the second flared portion 106 and/or to define and/or support the body portion 105. The first forming portion 600 may have a first tubular body portion 620 and a first enlarged end portion 610, wherein the first enlarged end portion 610 may be used to form and/or define the first flared portion 104. The second forming portion 700 may have a second tubular body portion 720 and a second enlarged end portion 710, wherein the second enlarged end portion 710 may be used to form and/or define the second flared portion 106. In some embodiments, the first forming portion 600 may be separate and distinct from the second forming portion 700. In some embodiments, the first forming portion 600 may be axially translatable relative to the second forming portion 700. In some embodiments, the first forming portion 600 and the second forming portion 700 may be monolithically formed as a single structure, wherein the first tubular body portion 620 and the second tubular body portion 720 are joined together, are coaxial with each other, and/or are coextensive.

A forming collar 800 may be configured to be disposed over the first tubular body portion 620 and/or the second tubular body portion 720, as seen in FIG. 10. The forming collar 800 may include an outer wall 810 and an inner wall 820, which collectively define a bowl-forming portion of the forming collar 800 having an annular and/or tubular structure and a lumen disposed therein and/or extending therethrough. The forming collar 800 may include a tip 830 and a body portion 840 disposed opposite the tip 830 relative to the bowl-forming portion. The body portion 840 may have an outer diameter that is greater than an outer diameter of the tip 830.

In some embodiments, the outer wall 810 of the bowl-forming portion may be tapered radially outward from the tip 830 of the bowl-forming portion toward the body portion 840 of the forming collar 800. In some embodiments, the outer wall 810 of the bowl-forming portion may be curved radially outward toward the body portion 840 of the forming collar 800. In some embodiments, the outer wall 810 of the bowl-forming portion may be conically shaped, with the outer wall 810 of the bowl-forming portion extending radially outward toward the body portion 840 of the forming collar 800. In some embodiments, the inner wall 820 of the bowl-forming portion may be tapered radially outward from the tip 830 of the bowl-forming portion toward the body portion 840 of the forming collar 800. In some embodiments, the inner wall 820 of the bowl-forming portion may be curved radially outward toward the body portion 840 of the forming collar 800. In some embodiments, the inner wall 820 of the bowl-forming portion may be conically shaped, with the inner wall 820 of the bowl-forming portion extending radially outward toward the body portion 840 of the forming collar 800. In some embodiments, the inner wall 820 may be generally parallel to the outer wall 810.

In some embodiments, the forming collar 800 may be formed as a unitary monolithic structure. In some embodiments, the forming collar 800 may be formed from a plurality of pieces. In some embodiments, the plurality of pieces may be complimentary to each other and/or may be interlocking with each other. In some embodiments, the plurality of pieces may be individually movable relative to each other.

The method may include disposing the forming collar 800 over, about, and/or around the body portion 105 of the expandable framework 110 between the first flared portion 104 and the second flared portion 106. In at least some embodiments, the tip 830 of the forming collar 800 may be oriented towards the first flared portion 104 and/or the first forming portion 600 of the forming mandrel. In some embodiments, the tip 830 of the forming collar 800 may be oriented towards the second flared portion 106 and/or the second forming portion 700 of the forming mandrel. The forming collar 800 and/or the tip 830 may be axially translatable relative to the forming mandrel, the first forming portion 600, and/or the second forming portion 700.

Figure 11:
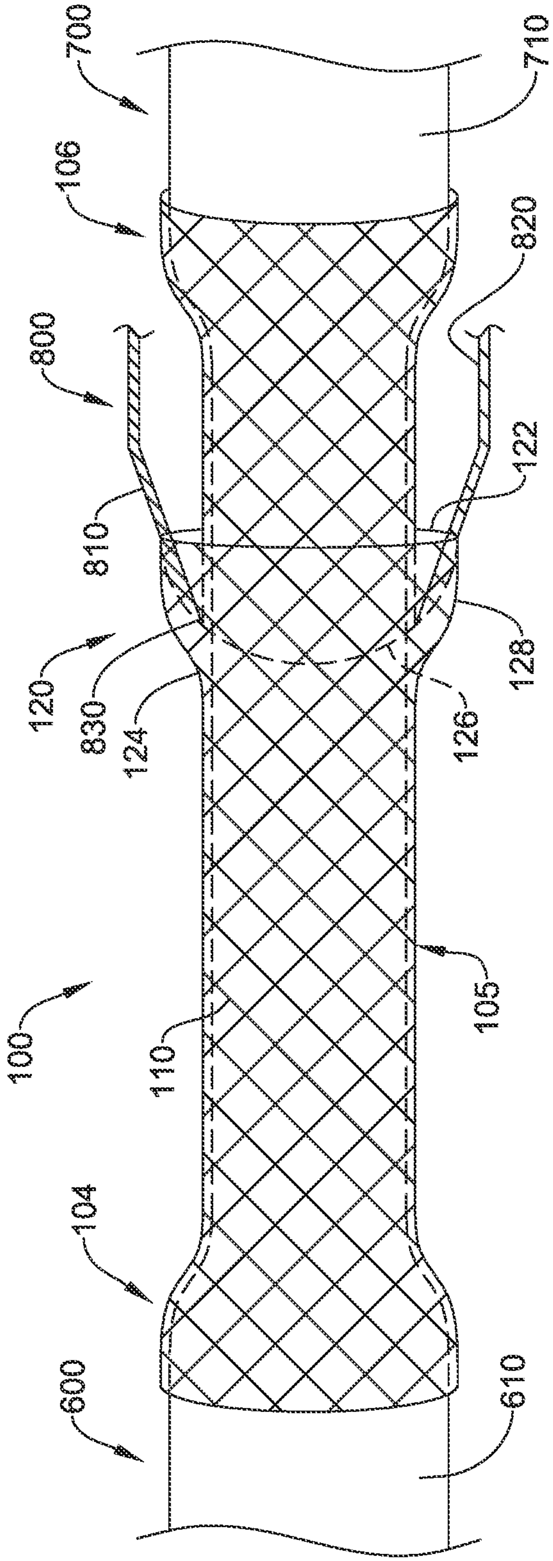

The method may include translating the first forming portion 600, the second forming portion 700, and/or the forming collar 800 axially relative to each other to urge a portion of the body portion 105 of the expandable framework 110 over the outer wall 810 of the forming collar 800 to form the bowl portion 120 of the expandable framework 110, as seen in FIG. 11 (where the forming collar 800 is shown in cross-section). In some embodiments, the forming collar 800 may be translated along and/or relative to the first tubular body portion 620 of the first forming portion 600. In some embodiments, the forming collar 800 may be axially translated toward the first enlarged end portion 610 of the first forming portion 600. In some embodiments, the first enlarged end portion 610 of the first forming portion 600 may be translated toward the forming collar 800. In some embodiments, the forming collar 800 may be translated along and/or relative to the second tubular body portion 720 of the second forming portion 700. In some embodiments, the forming collar 800 may be axially translated away from the second enlarged end portion 710 of the second forming portion 700. In some embodiments, the second enlarged end portion 710 of the second forming portion 700 may be translated away from the forming collar 800. After translating the first forming portion 600, the second forming portion 700, and/or the forming collar 800 axially relative to each other to form the bowl portion 120, the tip 830 of the forming collar 800 may extend into the interior of the bowl portion 120 with an everted portion of the expandable framework 110 forming the double walled portion defining the bowl portion 120.

In some embodiments, after translating the first forming portion 600, the second forming portion 700, and/or the forming collar 800 axially relative to each other to form the bowl portion 120, the expandable framework 110 may extend continuously from the second flared portion 106 towards the first flared portion 104 within the forming collar 800, around the tip 830 of the forming collar 800, from the tip 830 of the forming collar 800 towards the second flared portion 106 along the outer wall 810 of the forming collar 800 to the outer rim 122 of the bowl portion 120, and from the outer rim 122 of the bowl portion 120 towards the first flared portion 104. In cross-section, the bowl portion 120 of the expandable framework 110 may form and/or have the appearance of a generally zig-zag shaped structure, depending on the orientation of the view of the cross-section. In other words, the expandable framework 110 may extend continuously from the body portion 105 of the endoprosthesis proximal of the bowl portion 120, along the outer wall of the bowl portion from the base 124 to the outer rim 122 of the bowl portion 120, evert back toward the base 124 to form the inner wall of the bowl portion 120, and then evert back to extend along the body portion 105 extending from within the interior of the bowl portion toward the distal end of the endoprosthesis 100 distal of the bowl portion 120.

The method may include heat treating the expandable framework 110 to set the expandable framework 110 in the deployed configuration. In at least some embodiments, the method may include heat treating the expandable framework 110 with the forming mandrel, the first forming portion 600, the second forming portion 700, and/or the forming collar 800 held in place relative to the expandable framework 110 (e.g., as shown in FIG. 11). Thus, the endoprosthesis 100 may be heat set to revert to the expanded, deployed configuration with the bowl portion 120 extending circumferentially around the body portion 105.

Upon removal from the forming mandrel, the endoprosthesis 100 and/or the expandable framework 110 may be elongated and/or radially compressed into the delivery configuration. In at least some embodiments, the endoprosthesis 100 and/or the expandable framework 110 may be constrained in the delivery configuration by the delivery device 10. In some embodiments, when unconstrained, the endoprosthesis 100 and/or the expandable framework 110 may be self-biased toward and/or to return to the deployed configuration. In some embodiments, when subjected to, exposed to, and/or raised to a predetermined temperature (e.g., normal internal body temperature, etc.), the endoprosthesis 100 and/or the expandable framework 110 may be self-biased toward and/or to return to the deployed configuration.

The method may further include disposing the polymeric cover 160 over at least a portion of the expandable framework 110. In some embodiments, the forming collar 800 may prevent the polymeric cover 160 from being applied to the inner surface 126 of the inner wall of the bowl portion 120, while permitting the polymeric cover 160 to be applied to the body portion 105 of the expandable framework 110 extending into the interior of the bowl portion 120. In some embodiments, after removing the endoprosthesis 100 and/or the expandable framework 110 from the forming mandrel, the method may include removing the polymeric cover 160 from the inner surface 126 of the inner wall of the bowl portion 120. In some embodiments, after removing the endoprosthesis 100 and/or the expandable framework 110 from the forming mandrel, the method may include removing the polymeric cover 160 from a portion of the body portion extending into the interior of the bowl portion 120. In some embodiments, prior to disposing this polymeric cover 160 over at least a portion of the expandable framework 110, the inner surface 126 of the inner wall of the bowl portion 120 may be masked to prevent the polymeric cover 160 from being applied to the inner surface 126 and/or to permit easy removal of the polymeric cover 160 from the inner surface 126 without disturbing and/or damaging the polymeric cover 160 disposed on and/or over other portions of the expandable framework 110. In some embodiments, prior to disposing this polymeric cover 160 over at least a portion of the expandable framework 110, a portion of the body portion extending into the interior of the bowl portion 120 may be masked to prevent the polymeric cover 160 from being applied to that portion of the body portion 120 without disturbing and/or damaging the polymeric cover 160 disposed on and/or over other portions of the expandable framework 110.

In some embodiments, the polymeric cover 160 may be disposed over at least a portion of the expandable framework 110 after removing the endoprosthesis 100 and/or the expandable framework 110 from the forming mandrel and elongating the endoprosthesis 100 and/or the expandable framework 110 such that the inner surface 126 and/or inner wall of the bowl portion 120 is not everted within the outer surface 128 and/or the outer wall of the bowl portion 120. For example, as shown in FIG. 12, after heat setting the expandable framework 110 to include the bowl portion 120, the expandable framework 110 may be elongated over a coating mandrel 900 such that the inner wall of the bowl portion 120 is no longer everted within the outer wall of the bowl portion 120. Thereafter, the polymeric cover 160 may be selectively applied to (e.g., sprayed on) the length of the expandable framework 110 except for the portion of the elongate framework 110 within the bowl portion 120 configured to allow fluid to pass therethrough into the lumen of the endoprosthesis 100, such as the portion of the inner surface 126 of the inner wall of the bowl portion 120 and/or the portion of the body portion 105 extending into the interior of the bowl portion 120, as described above. In some embodiments, the polymeric cover 160 may be disposed over the entire endoprosthesis 100 and/or the entire expandable framework 110 and then the polymeric cover 160 may be removed from select cells along the portion configured to have open cells to allow fluid to flow therethrough into the interior of the endoprosthesis 100 within the bowl portion 120. In other instances, the endoprosthesis 100 and/or the expandable framework 110 may be returned to the deployed configuration and the polymeric cover 160 may be removed from the inner surface 126 of the inner wall of the bowl portion 120 and/or the portion of the body portion 105 extending into the interior of the bowl portion 105. In some embodiments, the inner surface 126 of the inner wall of the bowl portion 120 and/or the portion of the body portion extending into the interior of the bowl portion 105 may be masked prior to disposing the polymeric cover 160 over the entire endoprosthesis 100 and/or the entire expandable framework 110. Thus the polymeric cover 160 may include a first coating portion 162 discontinuous with a second coating portion 164, with an uncoated portion of the expandable framework 110 extending therebetween. The uncoated portion of the expandable framework 110 will be located within the interior of the bowl portion 120 when the expandable framework 110 reverts back to the deployed configuration. For example, the first coating portion 162 may extend along the body portion 105 proximal of the bowl portion 105 and the outer wall of the bowl portion 105, and the second coating portion 164 may extend along the body portion 105 distal of the bowl portion 105. The uncovered portion of the expandable framework 110 may extend circumferentially around the entire circumference of the expandable framework 110, or a portion thereof, if desired.

The materials that can be used for the various components of the endoprosthesis and the various elements thereof disclosed herein may include those commonly associated with medical devices. For simplicity purposes, the following discussion makes reference to the endoprosthesis. However, this is not intended to limit the devices and methods described herein, as the discussion may be applied to other elements, members, components, or devices disclosed herein, such as, but not limited to, the expandable framework, the bowl portion, the body portion, the polymeric cover, and/or elements or components thereof.

In some embodiments, the endoprosthesis and/or components thereof may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof, or any other suitable material.

In some embodiments, a linear elastic and/or non-superelastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the endoprosthesis and/or components thereof may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the endoprosthesis in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the endoprosthesis to achieve the same result.

In some embodiments, a degree of Magnetic Resonance Imaging (MRI) compatibility is imparted into the endoprosthesis and/or other elements disclosed herein. For example, the endoprosthesis, and/or components or portions thereof, may be made of a material that does not substantially distort the image and create substantial artifacts (i.e., gaps in the image). Certain ferromagnetic materials, for example, may not be suitable because they may create artifacts in an MRI image. The endoprosthesis or portions thereof may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the endoprosthesis and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the endoprosthesis and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum, or a Ni—Co—Cr-based alloy. The yarns may further include carbon, glass, or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible and implantable prosthesis and, more particularly, a vascular structure having desirable properties.

In some embodiments, the endoprosthesis and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); antiproliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An endoprosthesis, comprising:

an expandable framework having a lumen extending from a first end of the expandable framework to a second end of the expandable framework, the expandable framework including:

a body portion disposed between the first end and the second end, and a bowl portion disposed along the body portion between the first end and the second end; and a polymeric cover disposed on at least a portion of the expandable framework;

wherein the bowl portion extends radially outward from the body portion;

wherein the polymeric cover is disposed over the expandable framework from the first end to the second end of the expandable framework including the body portion and an outer surface of the bowl portion, except that an inner surface of the bowl portion within an interior of the bowl portion is devoid of the polymeric cover to permit fluid to flow from the interior of the bowl portion through the expandable framework into the lumen at a location between the first end and the second end.

2. The endoprosthesis of claim 1, wherein the polymeric cover includes a first portion extending from the first end toward the bowl portion and a second portion extending from the second end towards the bowl portion.

3. The endoprosthesis of claim 2, wherein the second portion of the polymeric cover extends into the interior of the bowl portion.

4. The endoprosthesis of claim 2, wherein the first portion of the polymeric cover extends along the outer surface of the bowl portion.

5. The endoprosthesis of claim 2, wherein the first portion of the polymeric cover longitudinally overlaps the second portion of the polymeric cover.

6. The endoprosthesis of claim 5, wherein the first portion is spaced apart radially outward from the second portion where the first portion of the polymeric cover longitudinally overlaps the second portion of the polymeric cover.

7. The endoprosthesis of claim 1, wherein the bowl portion is integrally formed with the body portion.

8. The endoprosthesis of claim 7, wherein the bowl portion includes an outer wall and an inner wall everted into the interior of the bowl portion from the outer wall, wherein the outer wall defines the outer surface of the bowl portion and the inner wall defines the inner surface of the bowl portion.

9. The endoprosthesis of claim 8, wherein the inner wall of the bowl portion is disposed radially outward of the body portion.

10. The endoprosthesis of claim 1, wherein the bowl portion includes an outer circumferential rim spaced radially outward from the body portion.

11. The endoprosthesis of claim 10, further comprising at least one radiopaque marker disposed along the outer circumferential rim.

12. The endoprosthesis of claim 1, wherein the bowl portion includes an open end facing toward the second end.

13. The endoprosthesis of claim 1, wherein the expandable framework includes only a single bowl portion.

14. An endoprosthesis, comprising:

an expandable framework including:

a body portion disposed between a first end and a second end, and only a single bowl portion disposed along the body portion; and a polymeric cover disposed on at least a portion of the expandable framework;

wherein the bowl portion includes an inner surface and an outer surface spaced apart radially outward from the inner surface;

wherein the bowl portion extends radially outward from the body portion;

wherein the inner surface of the bowl portion is devoid of the polymeric cover.

15. The endoprosthesis of claim 14, wherein the polymeric cover includes a first portion and a second portion discontinuous with the first portion, the first portion extending from the first end toward the bowl portion and along the outer surface of the bowl portion, and the second portion extending from the second end towards the bowl portion and into an interior of the bowl portion.

16. An endoprosthesis, comprising:

an expandable framework including:

a body portion disposed between a first end and a second end, and a bowl portion disposed along the body portion; and a polymeric cover disposed on at least a portion of the expandable framework;

wherein the bowl portion includes an inner surface and an outer surface spaced apart radially outward from the inner surface;

wherein the bowl portion extends radially outward from the body portion;

wherein the inner surface of the bowl portion is devoid of the polymeric cover;

wherein the polymeric cover includes a first portion and a second portion discontinuous with the first portion, the first portion extending from the first end toward the bowl portion and along the outer surface of the bowl portion, and the second portion extending from the second end towards the bowl portion and into an interior of the bowl portion.

* * * * *